(12) United States Patent
Pellegrino et al.

(10) Patent No.: US 6,907,884 B2
(45) Date of Patent: Jun. 21, 2005

(54) METHOD OF STRADDLING AN INTRAOSSEOUS NERVE

(75) Inventors: Richard Pellegrino, Mendon, MA (US); Paula Papineau, West Bridgewater, MA (US); John S. Crombie, East Hanover, NJ (US); Samit Patel, Maple Shade, NJ (US); Thomas Ryan, Flemington, NJ (US)

(73) Assignee: Depay Acromed, Inc., Raynham, MA (US)

( * ) Notice: Subject to any disclaimer, the term of this patent is extended or adjusted under 35 U.S.C. 154(b) by 288 days.

(21) Appl. No.: 10/260,879

(22) Filed: Sep. 30, 2002

(65) Prior Publication Data

US 2004/0064137 A1 Apr. 1, 2004

(51) Int. Cl.[7] ................................................ A61B 19/00
(52) U.S. Cl. ........................................ 128/898; 606/41
(58) Field of Search ...................... 128/898; 606/32–52

(56) References Cited

U.S. PATENT DOCUMENTS

| | | | |
|---|---|---|---|
| 3,845,771 A | 11/1974 | Vice | |
| 4,754,757 A | 7/1988 | Feucht | |
| 5,098,431 A | 3/1992 | Rydell | |
| 5,161,533 A | 11/1992 | Prass et al. | |
| 5,433,739 A | 7/1995 | Sluijter et al. | |
| 5,443,463 A | 8/1995 | Stern | |
| 5,540,684 A | 7/1996 | Hassler, Jr. | |
| 5,630,426 A | 5/1997 | Eggers et al. | |
| 5,647,871 A | 7/1997 | Levine et al. | |
| 5,697,281 A | 12/1997 | Eggers et al. | |
| 5,935,123 A | 8/1999 | Edwards et al. | |
| 6,073,051 A | 6/2000 | Sharkey et al. | |
| 6,099,514 A | 8/2000 | Sharkey et al. | |
| 6,139,545 A | 10/2000 | Utley et al. | |
| 6,146,380 A | 11/2000 | Racz et al. | |
| 6,149,620 A | 11/2000 | Baker et al. | |
| 6,241,725 B1 | 6/2001 | Cosman | |
| 6,264,651 B1 | 7/2001 | Underwood et al. | |
| 6,277,122 B1 | 8/2001 | McGahan et al. | |
| 6,283,961 B1 | 9/2001 | Underwood et al. | |

(Continued)

FOREIGN PATENT DOCUMENTS

| | | |
|---|---|---|
| EP | 80301764.9 A2 | 12/1981 |
| EP | 1059067 A1 | 12/2000 |
| EP | 1 059 067 A | 12/2000 |
| WO | WO 01 57655 A | 8/2001 |
| WO | WO 01/57655 A2 | 9/2001 |
| WO | 02/28302 A1 | 4/2002 |
| WO | WO 02 054941 A | 7/2002 |

OTHER PUBLICATIONS

Dupuy, AJR:175, Nov. 2000, pp. 1263–1267.
Tillotson, Investigative Radiology, Nov. 1989 pp. 888–892.
Cosman, Neurosurgery, 15(6), 1984, pp. 945–950.
Goldberg, Acad. Radiol., 1995; 2: 399–404.
Rosenthal, Sem. Musculoskeletal Radiology, vol. 1, No. 2, 1997, pp. 265–272.
Solbati, Interventional Radiology 1997, 205, pp. 367–373.
U.S. Appl. No. 10/259,689, DePuy AcroMed, Inc. Patent Application DEP–0807.
Massad, Malek M.D. et al.; Endoscopic Thoracic Sympathectomy: Evaluation of Pulsatile Laser, Non–Pulsatile Laser, and Radiofrequency–Generated Thermocoaguation; Lasers in Surgery and Medicine; 1991; pp 18–25.
EP Search Report dated Jan. 14, 2004 for EPO Appl. No. EP 03 25 6168.

Primary Examiner—Roy D. Gibson
Assistant Examiner—Pete Vrettakos
(74) Attorney, Agent, or Firm—Thomas M. DiMaure

(57) ABSTRACT

This invention relates to a method of straddling an intraosseous nerve with an energy transmitting device to improve the therapeutic treatment of the nerve.

28 Claims, 32 Drawing Sheets

U.S. PATENT DOCUMENTS

| | | |
|---|---|---|
| 6,287,304 B1 | 9/2001 | Eggers et al. |
| 6,312,426 B1 | 11/2001 | Goldberg et al. |
| 6,468,274 B1 | 10/2002 | Alleyne et al. |
| 6,478,793 B1 * | 11/2002 | Cosman et al. ............... 606/34 |
| 6,736,835 B2 * | 5/2004 | Pellegrino et al. ............ 607/96 |
| 2001/0029370 A1 | 10/2001 | Hodva et al. |
| 2001/0047167 A1 | 11/2001 | Geggeness |
| 2002/0026186 A1 | 2/2002 | Woloszko et al. |

* cited by examiner

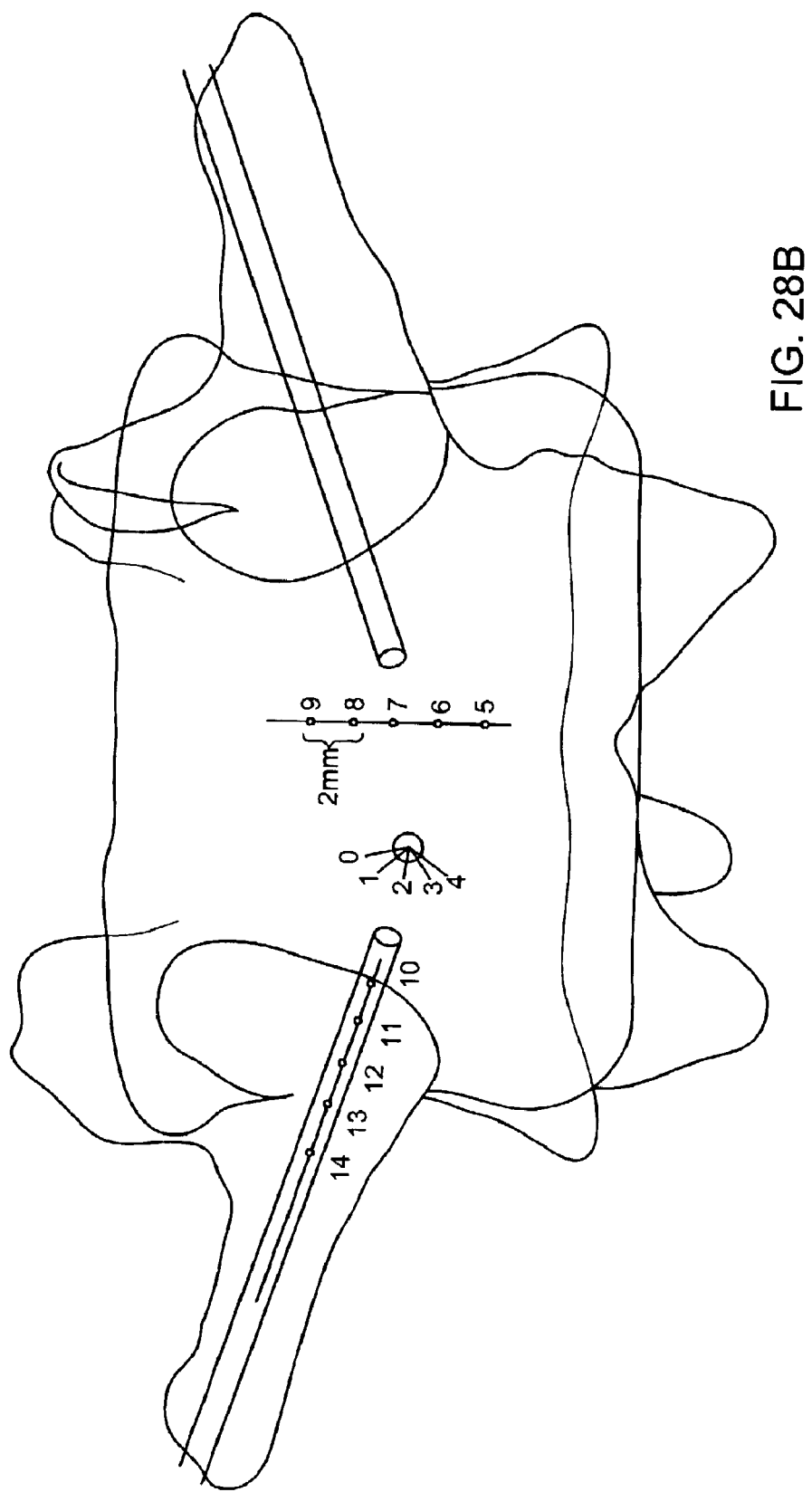

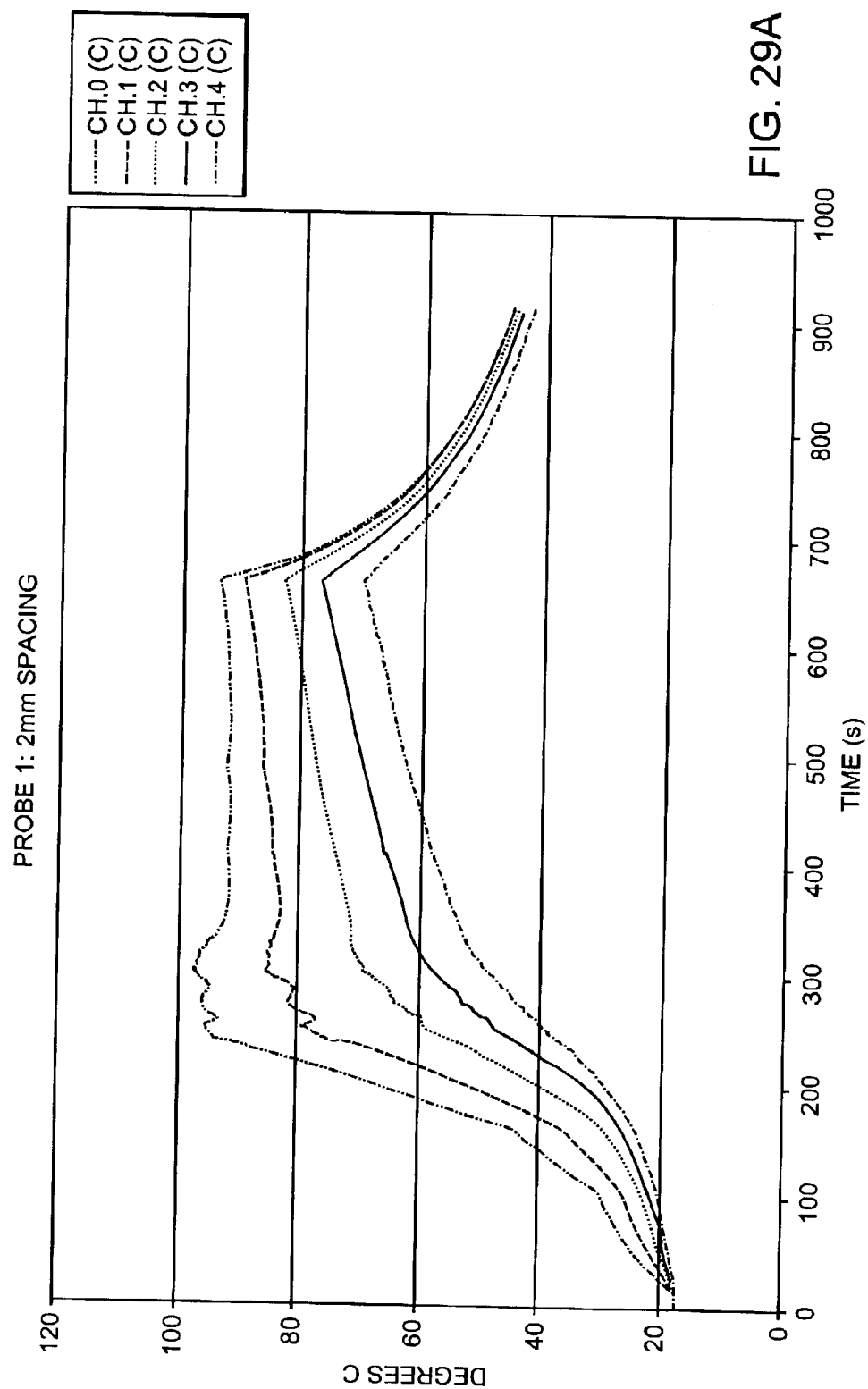

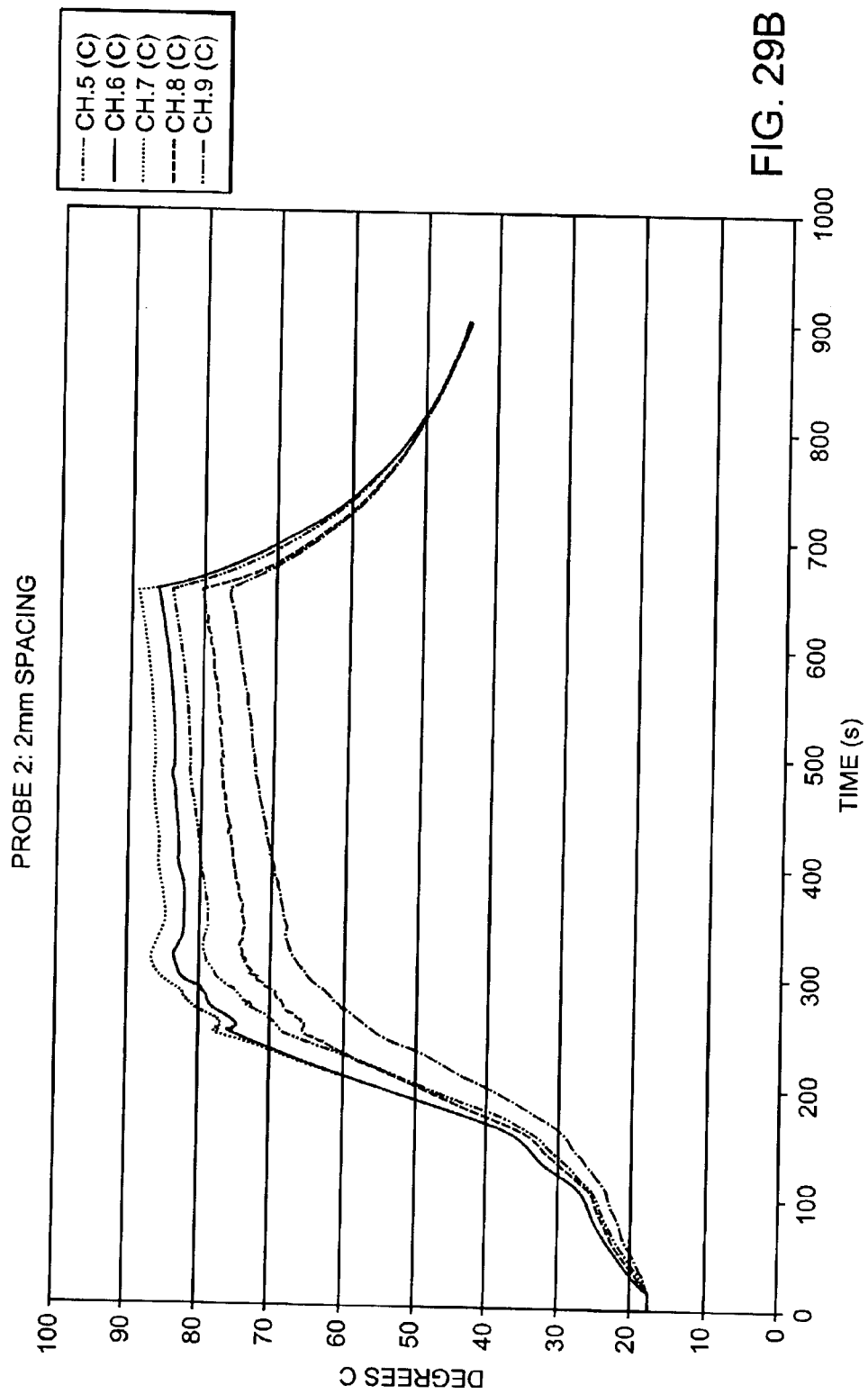

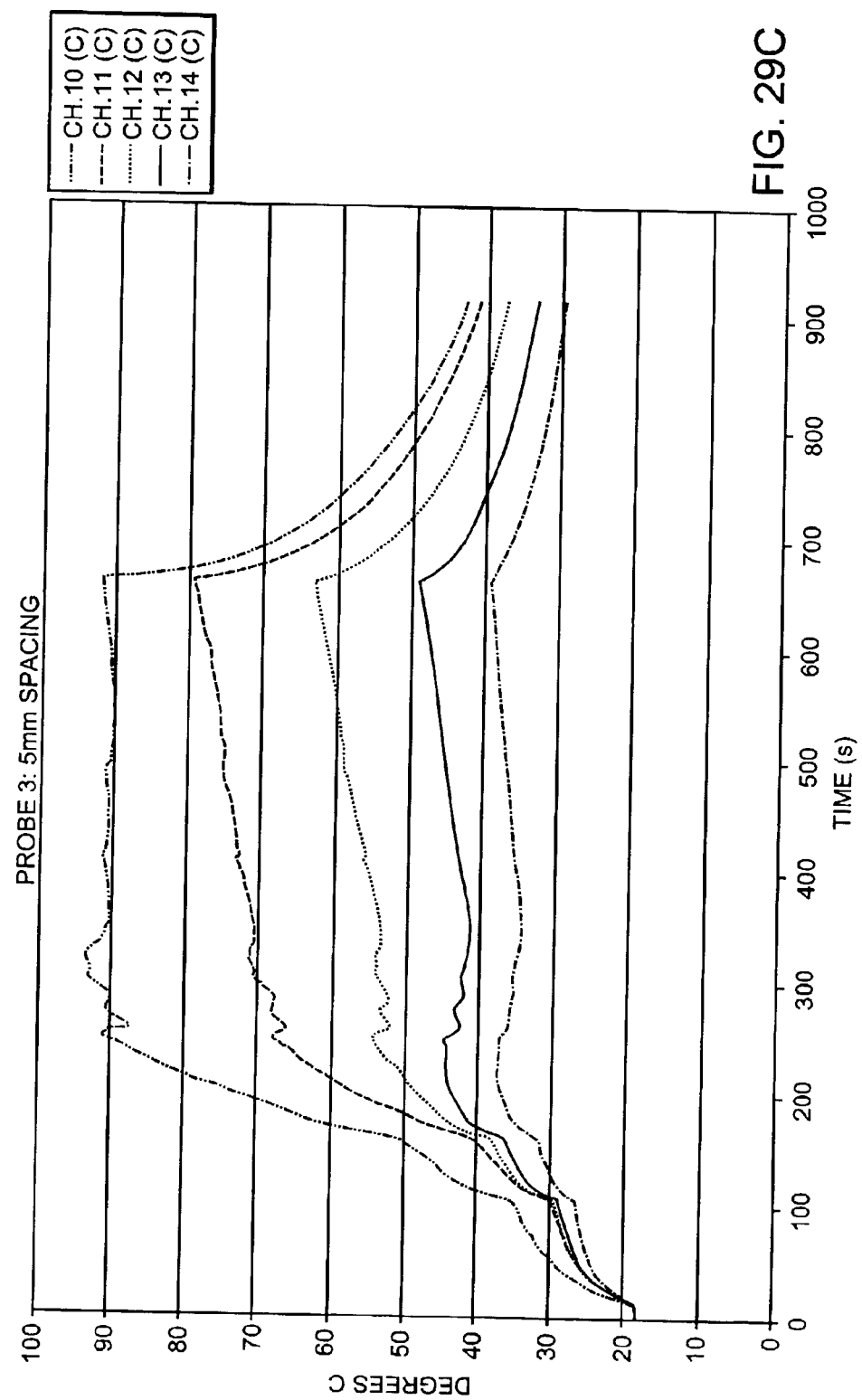

METHOD OF STRADDLING AN INTRAOSSEOUS NERVE

RELATED APPLICATIONS

This application is related to U.S. patent application Ser. No. 10/259,689, filed Sep. 30, 2002, entitled "Novel Device for Advancing a Functional Element Through Tissue", the specification of which is incorporated by reference.

BACKGROUND OF THE INVENTION

In an effort to reduce back pain through early intervention techniques, some investigators have focused upon nerves contained within the vertebral bodies which are adjacent the problematic disc.

For example, PCT Patent Publication No. WO 01/0157655 ("Heggeness") discloses ablating nerves contained within the vertebral body by first boring into the vertebral body with a nerve ablation device, placing the tip of the device in close proximity to the nerve, and then ablating the nerves with the tip. Heggeness discloses using laser devices, electricity transmitting devices, fluid transmitting devices and thermal devices, and devices for carrying either chemotherapeutic or radioactive substances as candidate nerve ablation devices.

In describing techniques using electricity transmitting devices, Heggeness discloses "raising the temperature of tip 24 such that the intraosseous nerve is ablated by the heat generated by electrical current passing through tip." See Heggeness at 8, 28.

Heggeness further discloses multiple methods of accessing the intraosseous nerve (ION). However, each of these methods essentially disclose either i) boring a straight channel into the vertebra such that placement of an electrode tip near the end of that channel will bring the electrode tip sufficiently close to the ION to effect its ablation, or ii) accessing the basivertebral nerve (BVN) via the vertebral foramen. None of these techniques recognize how to effectively carry out nerve ablation when the precise locations of the ION is unknown, or when the electrode tip can not be maneuvered relatively close to the ION.

EPO Patent Published Patent Application No. EP 1 059067 A1 ("Cosman") discloses ablative treatment of metastatic bone tumors, including those within the spine. Pain relief is reportedly achieved by penetrating the bone wall with a suitable probe, and applying heat through the probe to ablate either the bone tumor or the tissue near the bone tumor. Cosman teaches the use of both monopolar and bipolar probes in this application. Cosman also teaches that the treatment may also be used to ablate the nerves and nerve ramifications in and/or around the bone to desensitize them against farther tumor encroachment. See Cosman at col. 11, lines 7–11.

However, monopolar approaches require the use of a grounding pad beneath the patient and allows energy to flow from the probe and to dissipate in the surrounding tissue. Because the path by which the energy flows from a monopolar probe to its corresponding pad is uncontrolled, the energy may undesirably flow through sensitive tissue, such as the spinal cord. Since this method may cause undesired local muscle or nerve stimulation, it may be difficult or dangerous to operate in sensitive areas of the human body.

Cosman discloses devices whose electrodes can deviate from the axis of the access channel. In particular, Cosman discloses steerable tips, spring-like electrodes that take a straight shape within the catheter and then curve upon exiting the catheter. Cosman discloses that the curved portion of the electrode may be a rigid and rugged permanent curve, or it may be a flexible configuration so that it can be steered, pushed or guided by the clinician to be positioned at various location. See Cosman at col. 8, lines 40–50). Cosman discloses that electrodes may comprise tubing made of elastic or super-elastic metal such as a spring steel or nitonol tubing so that the electrode can be inserted into straight segments of the cannula and still describes a curved path when the curved portion emerges from the opening. See Cosman at col. 10, lines 11–16. Cosman also discloses an electrode having a flexible but steerable tip which can define an arc, as set by the physician. See Cosman at col. 14, line 3.

In sum, Heggeness and Cosman disclose methods of treating that assume the tip of the electrode can be directed substantially to the target tissue.

A few investigators have examined the effectiveness of heating bone with monopolar RF electrodes. DuPuy, *AJR:* 175, November 2000, 1263–1266 noted decreased heat transmission at a 10 mm distance from the electrode through cancellous bone in ex vivo studies. DuPuy notes that local heat sinks from the rich epidural venous plexus and cerebrospinal fluid pulsations may account for the decreased heat transmission in cancellous bone. Tillotson, *Investigative Radiology,* 24:11, November 1989, 888–892, studied the percutaneous ablation of the trigeminal ganglion using RF energy, and found that bone marrow necrosis was limited to a sphere of about 1 cm in diameter, regardless of the probe size and duration of heating. Tillotson further reports that Lindskog showed that the transmission of heat within bone is sharply limited by blood flow, and that lethal temperatures cannot be sustained over great distances.

In sum, these investigators appear to report that the well-vascularized nature of bone appears to limit the heating effect of RF electrodes to a distance of less than about 0.5 cm from the tip.

U.S. Pat. No. 6,312,426 ("Goldberg") discloses a system of RF plate-like electrodes for effecting large, uniform, and extended ablation of the tissue proximate the plate-like electrodes. In some embodiments, the plate-like electrodes are placed on the surface of the body tissue, where the ablation is desired, and are configured to lie approximately parallel or opposing one another, such that they make a lesion by coagulating most of the body tissue volume between them. Goldberg appears to be primarily directed to the treatment of tumors. Goldberg states that one advantage of the system is that the surgeon need not determine the precise position of the tumor. See Goldberg at col. 3, line 59–60. Goldberg does not appear to specifically discuss the treatment of nerves.

U.S. Pat. No. 6,139,545 ("Utley") discloses a facial nerve ablation system including at least two spaced apart bi-polar probe electrodes spanning between them a percutaneous tissue region containing a facial nerve branch. Utley teaches that the size and spacing of the electrodes are purposely set to penetrate the skin to a depth sufficient to span a targeted nerve or nerve within a defined region. See col. 5, lines 44–47. Utley further teaches that the system makes possible the non-invasive selection of discrete motor nerve branches, which are small and interspersed in muscle, making them difficult to see and detect, for the purpose of specifically targeting them for ablation. See col. 2, lines 20–24. Utley does not disclose the use of such a system for the treatment of IONS, nor rigid probes, or deployable electrodes. The probes of Utley

SUMMARY OF THE INVENTION

In attempting to place an electrode in close proximity to the BVN, the present inventors have found the approaches disclosed in the teachings of the art to be somewhat problematic. In particular, although the location of the BVN is somewhat well known, the BVN is radiolucent and so its precise location can not be easily identified by an X-ray. Since the BVN is also extremely thin, knowingly placing the electrode in close proximity to the BVN may be problematic. Moreover, since conventional RF electrodes appear to heat only a fairly limited volume of bone, misplacement of the electrode tip vis-a-vis the BVN may result in heating a volume of bone that does not contain the BVN.

For example, and now referring to FIGS. 1 and 2, there is provided a representation of a treatment scheme involving the placement of a conventional bipolar electrode device in close proximity to the ION. In these FIGS., the ION is represented by the solid line identified as ION, while the vertically-disposed dotted lines identify the edges of the zone within which the practitioner believes the ION likely resides (i.e., the ION residence zone, or "IRZ"). As shown in FIGS. 1 and 2, if the ION is substantially in the center of the ION residence zone, then placement of the bipolar electrode either on the left hand boundary of the ION residence zone (as in FIG. 1) or substantially in the middle of the ION residence zone (as in FIG. 2) satisfactorily locates the electrodes in a region that allows the current flowing from the electrodes to flow across the ION. Since the current flowing across the ION may resistively and conductive heat the local bone tissue and the ION will be heated to therapeutically beneficial temperatures, these scenarios may provide beneficial treatment of the ION.

However, and now referring to FIG. 3, if the ION is substantially at the right edge of the ION residence zone, then placement of the bipolar electrodes on the left hand side of the ION residence zone fails to locate the electrodes in a region that allows the current flowing from the electrodes to flow across the ION. Accordingly, current flowing across the electrodes can not resistively heat the ION. Moreover, since bone is a heat sink that effectively limits the heat transport to about 0.5 cm, the heat produced by the electrodes may be effectively dissipated before it can reach the ION by conduction.

Similarly, and now referring to FIG. 4, if the ION is substantially at the left edge of the ION residence zone, then placement of the bipolar electrodes in the middle of the ION residence zone fails to locate the electrodes in a region that allows the current flowing from the electrodes to flow across the ION. Again current flowing across the electrodes can not resistively heat the ION, and the heat sink quality of bone may effectively dissipate the heat produced by the electrodes before it can reach the ION by conduction.

Moreover, even if the precise location of the BVN were known, it has been found to be difficult to access the posterior portion of the BVN from a transpedicular approach with a substantially straight probe.

Therefore, the present inventors set out to produce a system that allows the practitioner to heat the BVN without having to know the precise location of the BVN, and without having to precisely place the electrode tip next to the portion of the BVN to be treated.

The present invention relates to the production of a large but well-controlled heating zone within bone tissue to therapeutically treat an ION within the heating zone.

Now referring to FIGS. 5–6, there is provided a representation of an embodiment of the present invention in which electrodes E1 and E2 respectively disposed probes (not shown) therapeutically treat the ION. FIG. 5 provides a schematic representation of the electric field EF produced in the bone tissue by activation of the electrodes. In this case, the electric field is relatively thin. FIG. 6 provides a schematic representation of the total heating zone THZ produced by the electric field of FIG. 5 including both an inner resistive heating zone IR (represented by open circle) and an outer conductive heating zone OC (represented by closed circles). In this case, the inner resistive zone is produced by the joule heating of bone tissue disposed within the electric field EF, while the outer conductive zone is heated by conduction of heat from the resistive heating zone.

Still referring to FIG. 6, the present inventors have found that positioning the active and return electrodes of an energy-transmitting device in a manner that allows the electrodes to straddle the ION residence zone IRZ provides a large but well-controlled total heating zone (IR+OC) within bone tissue to therapeutically treat the ION within the heating zone. Since the total heating zone is large and the electrodes straddle the IRZ, there is a high level of confidence that a portion of the ION will be present within the total heating zone. Since the total heating zone is well controlled, there is no danger (as with monopolar systems) that current flowing from the active electrode will undesirably affect collateral tissue structures Now referring to FIG. 7, if the ION is in fact substantially in the center of the ION residence zone, then placement of the bipolar electrodes in a manner that straddles the ION residence zone allows the production a total heating zone between the electrodes that includes a portion of the ION therein.

Moreover, the present invention allows the practitioner to therapeutically treat the ION even when the ION is in fact located at the edges of the ION residence zone IRZ. Now referring to FIGS. 8 and 9, if the ION is located substantially at the right edge (as in FIG. 8) or the left edge (as in FIG. 9) of the ION residence zone IRZ, then placement of the bipolar electrodes in a manner that straddles the ION residence zone still allows the production a total heating zone between the electrodes that includes a portion of the actual ION therein.

Therefore, the straddling of the ION residence zone by the present invention satisfactorily locates the electrodes so that the total heating zone produced by the electrode activation includes the ION irrespective of the actual location of the ION within the ION residence zone IRZ, thereby guaranteeing that the electrodes will always heat the ION to therapeutically beneficial temperatures.

Therefore, in accordance with the present invention, there is provided a method of therapeutically treating a bone having an intraosseous nerve ION defining first and second sides of the bone, comprising the steps of:

a) inserting an energy device having an active and a return electrode into the bone,
b) placing the active electrode on the first side of the bone and the return electrode on the second side of the bone to define a total heating zone therebetween, and applying a sufficiently high frequency voltage between the active and return electrodes to generate a current therebetween to resistively heat the total heating zone sufficient to denervate the ION.

In addition, the present invention provides a very controlled total heating zone which exists substantially only between the paired electrodes. The ability of the present invention to both therapeutically heat the BVN with substantial certainty and to minimize the volume of bone tissue affected by the heating appears to be novel in light of the conventional bone-related technology.

Accordingly, the present invention is further advantageous because it allows the clinician to create a sufficiently large heating zone for therapeutically treating the ION without requiring direct access to the ION.

Thus, in preferred embodiments, the present invention is advantageous because:
1) it does not require knowing the precise location of the ION,
2) it does not require directly accessing the ION, and
3) its controlled heating profile allows the clinician to avoid heating adjacent structures such as the healthy adjacent cancellous bone tissue, the spinal cord or opposing vertebral endplates.

Accordingly, there is also provide a method of therapeutically treating a vertebral body having a BVN defining first and second sides of the vertebral body, comprising the steps of:
a) determining a BVN residence zone within which the BVN likely resides, the BVN residence zone having a first side and a second side,
b) inserting an energy device having an active and a return electrode into the vertebral body,
c) placing the active electrode on the first side of the residence zone and the return electrode on the second side of the residence zone to define a total heating zone therebetween, and
d) applying a sufficiently high frequency voltage between the active and return electrodes to generate a current therebetween to resistively heat the total heating zone to a temperature sufficient to denervate the BVN.

DESCRIPTION OF THE FIGURES

FIGS. 28a and 28b show the location of thermocouples T0–T14 within the vertebral body.

FIGS. 29a–c present the temperatures recorded by thermocouples T0–T14.

DETAILED DESCRIPTION OF THE INVENTION

For the purposes of the present invention, the "resistive heating zone" is the zone of bone tissue that is resistively heated due to an energy loss incurred by current travelling directly through the bone tissue. Resistive heating, "joule" heating and "near-field" heating may be used interchangeably herein. The "conductive heating zone" is the zone of bone tissue that is heated due to the conduction of heat from an adjacent resistive heating zone. The total heating zone THZ in a bone tissue includes both the resistive heating zone and the conductive heating zone. The border between the conductive and resistive heating zones is defined by the locations where the strength of the electric field is 10% of the maximum strength of the electric field between the electrodes. For the purposes of the present invention, the heating zones encompass the volume of bone tissue heated to at least 42° C. by the present invention. For the purposes of the present invention, the "first and second sides" of a vertebral body are the lateral—lateral sides intersected by the BVN.

The therapeutic treatment of the ION may be carried out in accordance with the present invention by resistive heating, conductive heating, or by hybrid heating.

Figure 1:
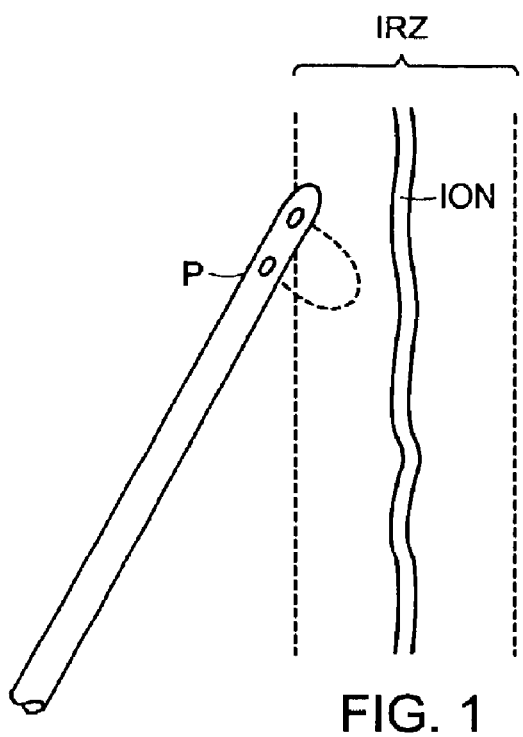
FIGS. 1 and 2 depict the treatment of the BVN with a conventional bipolar electrode.
Figure 2:
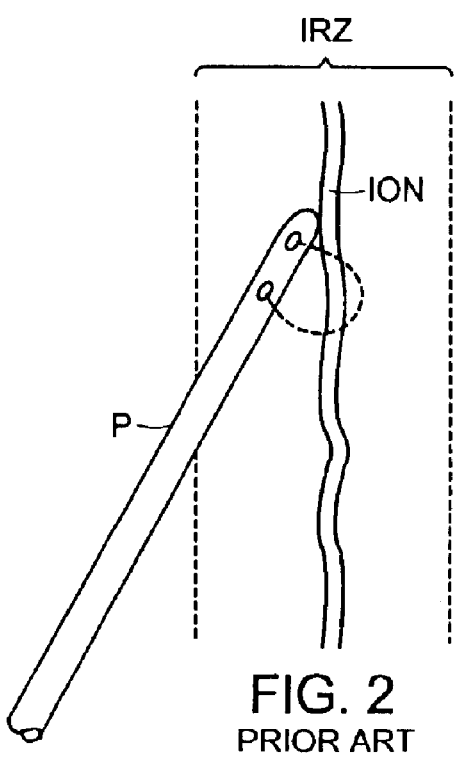
Figure 3:
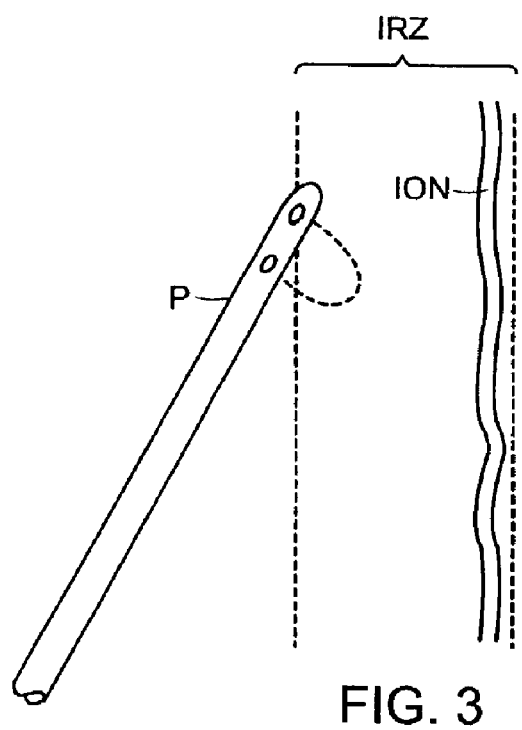
FIGS. 3 and 4 depict the difficulty of treating a BVN with a conventional bipolar electrode.
Figure 4:
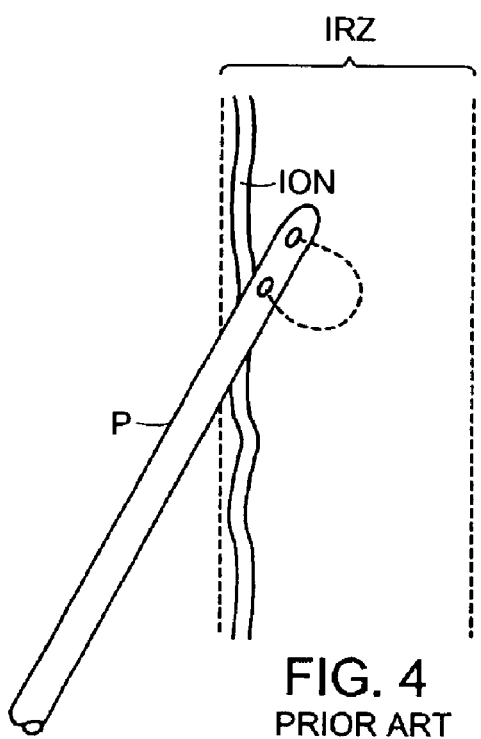
Figure 5:
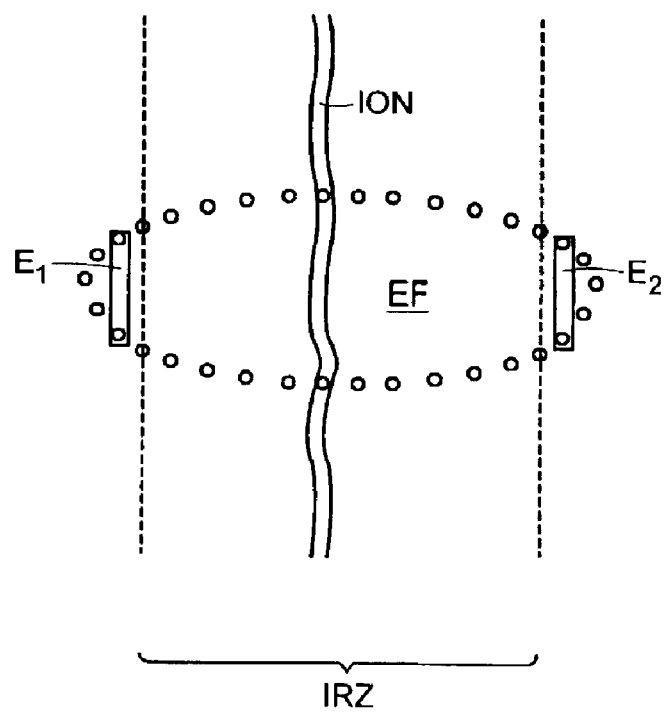
FIGS. 5–6 respectively depict top views of an electric field and a total heating zone produced within bone tissue by an embodiment of the present invention.
Figure 6:
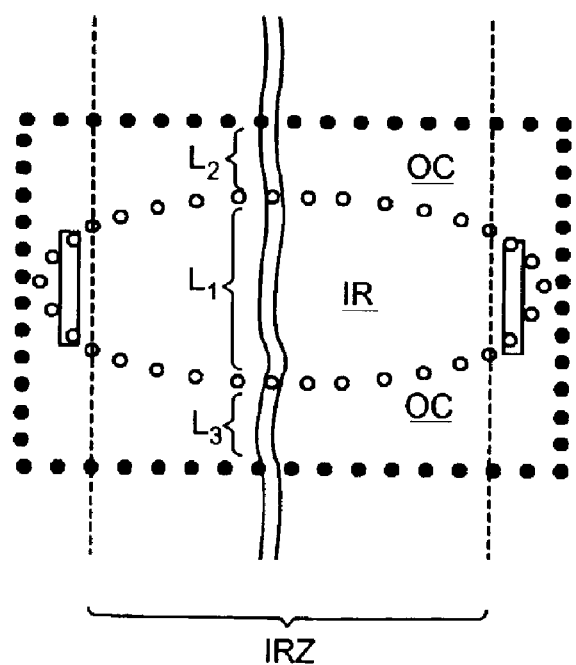
Figure 7:
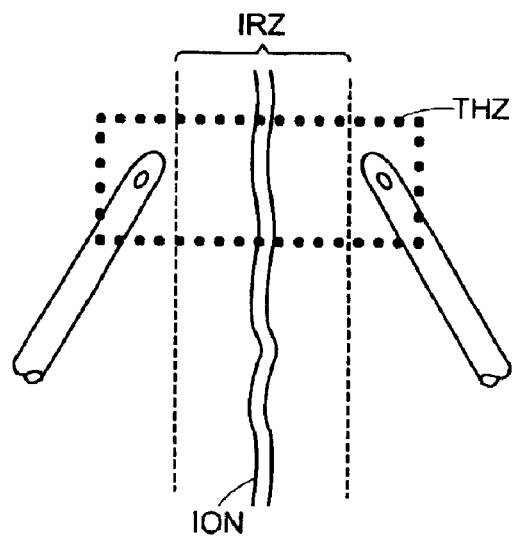
FIGS. 7–9 depict the treatment of the BVN with a bipolar electrode apparatus of the present invention.
Figure 8:
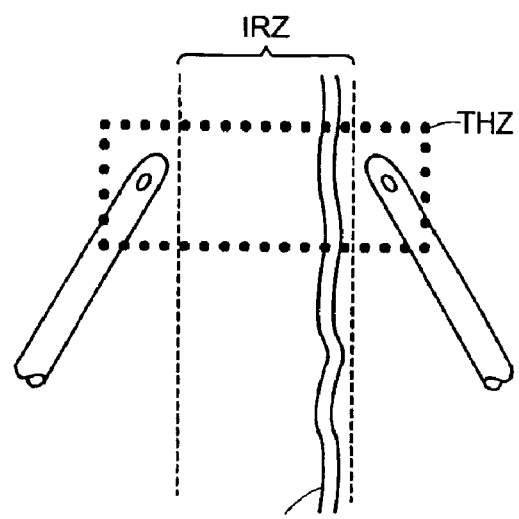
Figure 9:
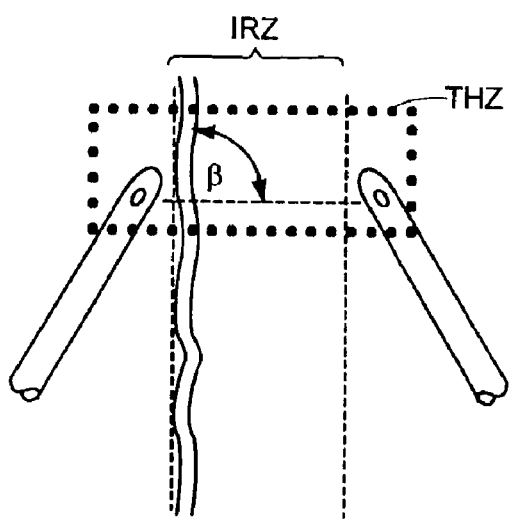

In some embodiments, the therapeutic heating of the ION is provided by both resistive and conductive heating. In some embodiments thereof, as in FIG. 6, the electrodes are placed such that the ION passes through resistive heating zone IR, so that length $L_1$ of the ION is therapeutically heated by bone tissue in the resistive heating zone IR and lengths $L_2$ and $L_3$ of the ION are therapeutically heated by the bone tissue in the conductive heating zone OC.

In embodiments wherein the therapeutic heating of the ION is provided substantially by both resistive and conductive heating, it is preferred that the length $L_1$ of the ION treated by resistive heating comprise at least 25% of the total therapeutically treated length of ION, more preferably at least 50%. In many embodiments, the peak temperature in the resistive heating zone IR is between 40° C. and 60° C. greater than the peak temperature in the conductive heating zone OC. Preferably, the peak temperature in the resistive heating zone IR is no more than 15° C. greater than the peak temperature in the conductive heating zone OC, more preferably no more than 10° C., more preferably no more than 5 degrees.

Figure 10A:
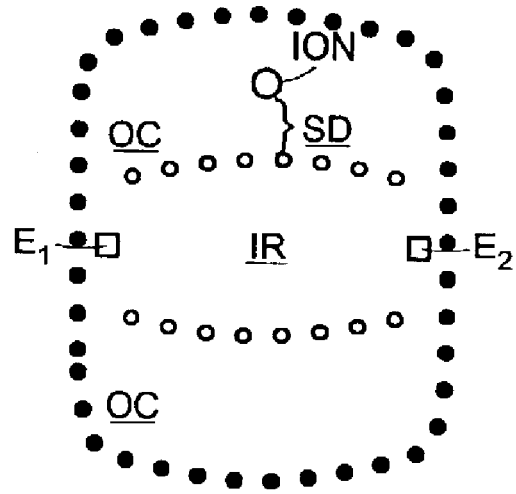
FIGS. 10a and 10b disclose anterior and upper cross-sectional views of a straddled ION that extends in a plane above the electrodes but within the total heating zone.
Figure 10B:
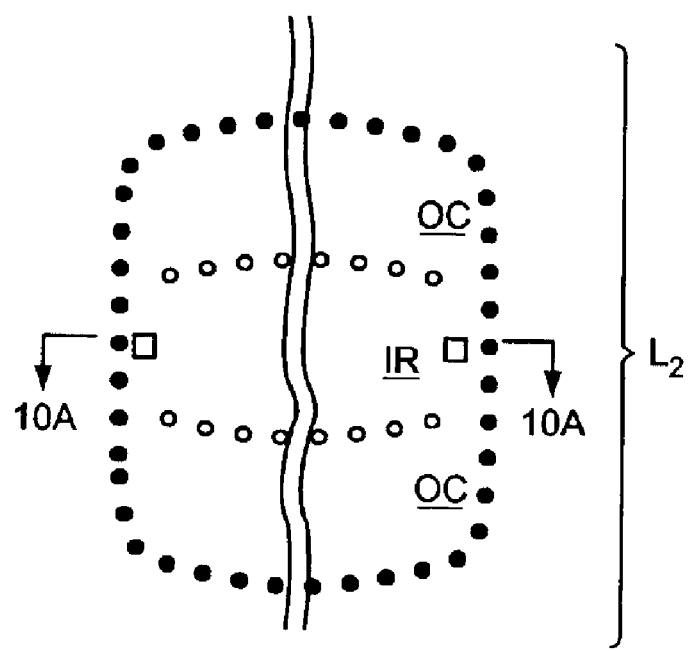

Now referring to FIGS. 10a and 10b, in some embodiments, the therapeutic heating of the ION is provided essentially by the conductive heating zone OC. This may occur when the ION is in fact located substantially far from the middle of the ION residence zone IRZ. In such an instance, the electrodes are placed such that the ION passes only through the conductive heating zone, so that length $L_2$ of the ION is therapeutically heated by bone tissue in the conductive heating zone OC.

In preferred embodiments thereof, it is desired that the separation distance SD between the ION and the resistive heating zone IR be no more than 1 cm. This is desired because the closer the ION is to the resistive heating zone, the higher the temperature experienced by the ION length $L_2$. More preferably, the separation distance is no more than 0.5 cm, more preferably no more than 0.2 cm.

Figure 11:
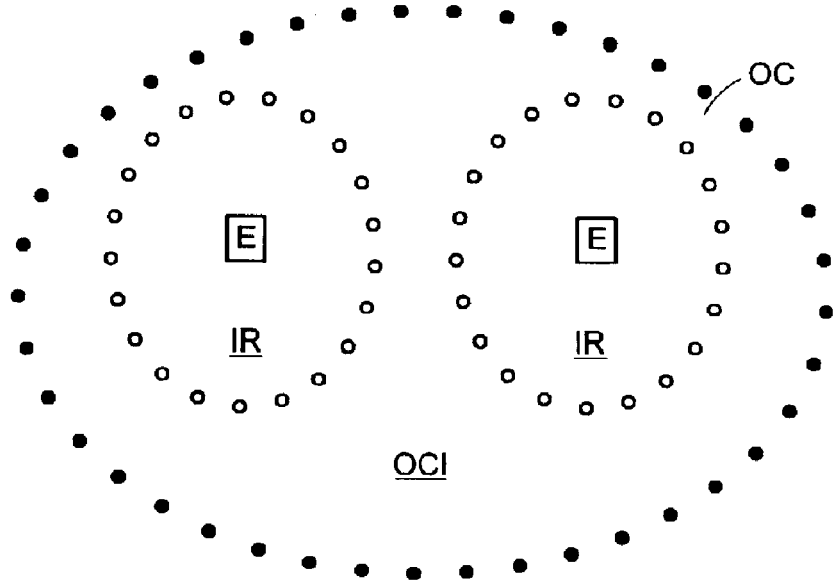
FIG. 11 is a cross-sectional anterior view of an embodiment of the present invention in which the total heating zone has dumb-bell type resistive heating zones.

In some embodiments, as in FIG. 10, the electric field is sufficiently strong to be located substantially continuously between the two electrodes. This typically occurs when the electrodes are very close together (i.e., no more than 5 mm apart). In others, however, as in FIG. 11, the electric field is relatively weak and so resides substantially only in the vicinity of the two electrodes. In such cases, and now referring to FIG. 11, inward energy flow from the resistive heating zones IR conductively heats the intermediate area of the conductive heating zone $OC_1$. Preferably, the peak temperature in the resistive heating zone IR is no more than 15° C. greater than the peak temperature in the intermediate conductive heating zone $OC_1$, more preferably no more than 10° C., more preferably no more than 5° C.

In preferred embodiments, the present invention is carried out via a dual probe system. In particular, the present invention preferably comprises an energy delivery device comprising a first probe having an active electrode and a second probe having a return electrode. Now referring to FIG. 12, this dual probe embodiment allows the surgeon to approach the BVN from separate sides of the vertebral body to easily straddle the IRZ with the electrodes. With such a device, the surgeon can place the first probe 601 having an active electrode 603 on a first side of the vertebral body and the second probe 611 having a return electrode 613 on a second side of the vertebral body, and then align the paired electrodes so that their activation produces a total heating zone that straddles the IRZ and therefore the BVN therein.

Since aligning the electrodes of such an apparatus to straddle the ION merely requires advancing the probes into the vertebral body, no complicated navigation is required. The present inventors have appreciated that, even if the location of the BVN were precisely known, conventional methods of accessing the BVN require either i) the BVN to be naturally located within the vertebral body so as to intersect the axis of the pedicle (Heggeness), or require a complicated probe configuration or navigation (such as those described by Cosman). Because the dual probe approach simply requires substantially linear advance of a pair of substantially straight probes, it is much simpler and/or much more robust than the conventional methods of accessing nerves in bone. Indeed, with this embodiment of the present invention, the clinician may now desirably access the vertebral body through the pedicles with substantially straight probes and have a high confidence that their activation can therapeutically treat the BVN.

Therefore, in accordance with the present invention, there is provided a method of therapeutically treating a vertebral body having a BVN, comprising the steps of:
a) providing an energy device having an active electrode having a first face and a return electrode having a second face into the vertebral body, and
b) placing the active electrode in the vertebral body to face a first direction,
c) placing the return electrode in the vertebral body to face a second direction, the first and second faces defining an angle 2δ of no more than 60 degrees, and
applying a sufficiently high frequency voltage difference between the active and return electrodes to generate a current therebetween to produce a total heating zone to therapeutically heat the BVN.

Therefore, in accordance with the present invention, there is provided a method of therapeutically treating a vertebral body having a BVN, comprising the steps of:
a) providing an energy device having an active electrode and a return electrode,
b) placing the active and return electrodes in the vertebral body to define an electrode axis, the axis forming an angle β of between 50 and 90 degrees with the BVN, and
c) applying a sufficiently high frequency voltage difference between the active and return electrodes to generate a current therebetween to produce a total heating zone to therapeutically heat the BVN.

Figure 13:
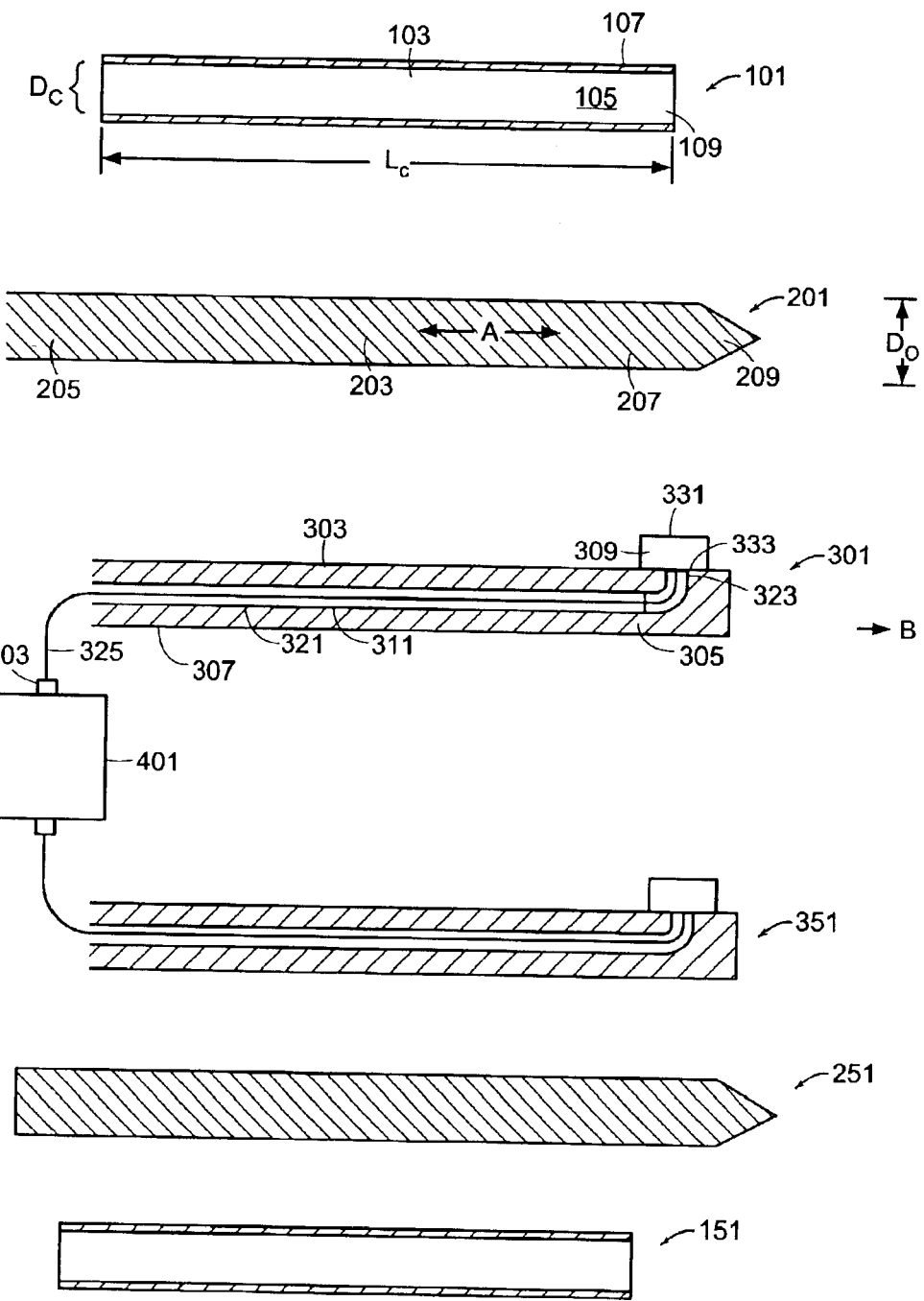
FIG. 13 discloses cross-sections of components of a preferred dual probe apparatus according to the present invention.

Now referring to FIG. 13, there is provided a preferred dual probe apparatus according to the present invention comprising first 101 and second 151 cannulae, first 201 and second 251 stylets, first 301 and second 351 probes, and a power supply 401 in electrical connection with the probes. For simplicity, only a single cannula, stylet and probe will be further described. However, the skilled artisan will appreciate that preferred embodiments use two sets of such devices.

Now referring to FIG. 13, cannula 101 comprises a shaft 103 having a longitudinal bore 105 therethrough defining an inner diameter $D_C$. Distal opening 109 of the cannula provides a working portal for the probe. It is further sized to allow the distal end of the probe to advance past the distal end 107 of the cannula. The length Lc of the cannula is sized to reach from the patient's skin to a location within the cancellous bone region of the target bone. Preferably, the cannula is made of a material selected from the group consisting of metal and polymer, and is preferably polymer. In many embodiments, the cannula is made of an insulating material in order to prevent stray current from the probe from contacting non-targeted tissue.

In some embodiments, the cannula is shaped so as to guide the probe towards the midline of the vertebral body. This inward guidance will help move the electrodes closer to the BVN. In some embodiments, at least a portion of the cannula bore is curved. In some embodiments, at least half of the length of the cannula bore is curved. In other embodiments, substantially only the distal end portion of the cannula bore is curved.

Stylet 201 comprises a shaft 203 having a longitudinal axis A and a proximal 205 and distal end 207. Disposed at the distal end of the shaft is a tip 209 adapted for boring or drilling through cortical bone. The outer diameter $D_O$ of the stylet shaft is preferably adapted to be received within the inner diameter $D_C$ of the cannula.

For the purposes of the present invention, the combination of the cannula and the stylet is referred to as a "cannulated needle". In some embodiments, access to the vertebral body is gained by first placing the stylet in the cannula to produce a cannulated needle, piercing the skin with the cannulated needle, and advancing the cannulated needle so that the stylet tip reaches a target tissue region within the cancellous portion of the vertebral body, and then withdrawing the stylet. At this point, the cannula is conveniently located at the target tissue region to receive a probe of the present invention.

Probe 301 comprises a shaft 303 having a longitudinal axis B, a distal end portion 305 and a proximal end portion 307. Disposed near the distal end portion of the probe is first electrode 309 having a first face 331 and a connection face 333. The probe is designed so that the connection face of the first electrode is placed in electrical connection with a first lead 403 of the power supply. In this particular embodiment, the shaft has a longitudinal bore 311 extending from the proximal end portion up to at least the first electrode. Disposed within the bore is a wire 321 electrically connected at its first end 323 to the first electrode and having a second end 325 adapted to be electrically connected to a first lead of a power supply.

Therefore, in accordance with the present invention, there is provided an intraosseous nerve denervation system, comprising:

a) a cannula having a longitudinal bore,
b) a stylet having an outer diameter adapted to be received within the longitudinal bore and a distal tip adapted to penetrate cortical bone, and
c) a first probe comprising:
  i) an outer diameter adapted to be received within the longitudinal bore, and
  ii) a first electrode, and
  iii) a lead in electrical connection with the first electrode.

In some embodiments, the outer surface of the probe is provided with depth markings so that the clinician can understand the extent to which it has penetrated the vertebral body.

In some embodiments in which a cannulated stylet is first inserted, the stylet is removed and the cannula remains in place with its distal opening residing in the target tissue while the probe is inserted into the cannula. In this embodiment, the cannula provides a secure portal for the probe, thereby insuring that the probe can enter the bone safely. This embodiment is especially preferred when the probe is made of a flexible material, or is shaped with an irregular cross-section that could undesirably catch on the bone during probe advancement into the bone.

In the FIG. 13 probe disclosed above, probe 301 has a blunt tip. In other embodiments, however, the probe carrying an electrode can be configured to possess a sharp distal tip having sufficient sharpness to penetrate cortical bone. With such a tip, the clinician can eliminate steps in the procedure that are related to either the stylet or the cannulated stylet, and thereby save time.

Figure 14:
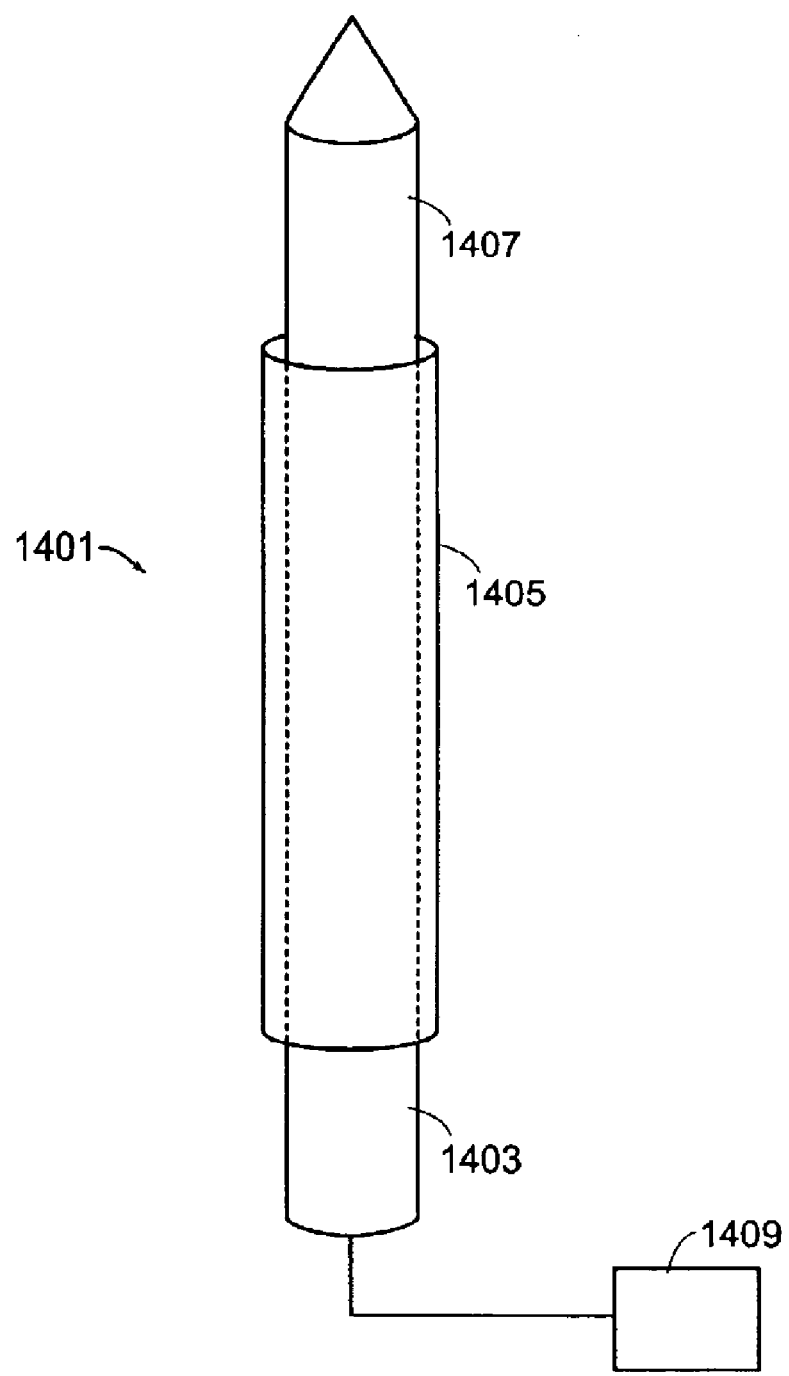
FIG. 14 discloses an embodiment of the present invention in which a portion of the probe shaft acts as an electrode.

Now referring to FIG. 14, in some embodiments, the electrode may include a portion of the probe shaft. For example, in the case of probe 1401, the probe comprises:

a) an inner electrically conductive shaft 1403 in electrical connection with a power supply 1409, and b) an outer insulating jacket 1405 wrapped around a portion of the shaft.

In this configuration, the placement of the jacket provides a distal uninsulated shaft portion 1407 that could be used as an electrode. Preferably, the distal uninsulated portion of the shaft has a length of between 3 mm and 8 mm, and is more preferably about 5 mm. In preferred embodiments thereof, the insulation is selected from the group consisting of polyimide tape, PTFE tape, and heat shrink tubing. Preferred thickness of the insulation range from about 0.00025 to 0.0005 inches.

In other embodiments using insulating jackets, the jacket has either a longitudinally extending slit or slot that exposes a longitudinal surface area of the underlying shaft, thereby producing either an essentially linear or an essentially planar electrode. In such embodiments, the distal end of the shaft may preferably be insulated. In other embodiments using insulating jackets, the insulated portion may comprises a proximal jacket and a distal jacket positioned to provide a space therebetween that exposes a surface area of the underlying shaft to produce the electrode. In some embodiments, the proximal and distal jacket substantially encircle the shaft to provide an annular electrode therebetween.

In some embodiments in which a cannulated stylet is used, both the stylet and the cannula are removed, and the probe is inserted into the hole created by the cannulated stylet. In this embodiment, the hole provides a large portal for the probe. This embodiment conserves the annulus of bone removed by the cannula, and so is preferred when the probe has a relatively large diameter (e.g., more than 8 mm in diameter).

In some embodiments in which a cannulated stylet is used, the cannula comprises at least one electrode In this embodiment, the cannula acts as the probe as well. With this embodiment, the clinician can eliminate steps in the procedure that are related to introducing a body into the cannula. In some embodiments, the outer surface of the cannula is provided with depth markings so that the clinician can understand the extent to which the cannula has penetrated the vertebral body.

In some embodiments in which a cannulated stylet is first inserted, the stylet comprises at least one electrode. In this embodiment, the stylet acts as the probe as well. With this embodiment, the clinician can eliminate steps in the procedure that are related to removing the stylet and introducing a body into the cannula. In some embodiments, the outer surface of the stylet is provided with depth markings so that the clinician can understand the extent to which it has penetrated the vertebral body.

Figure 12:
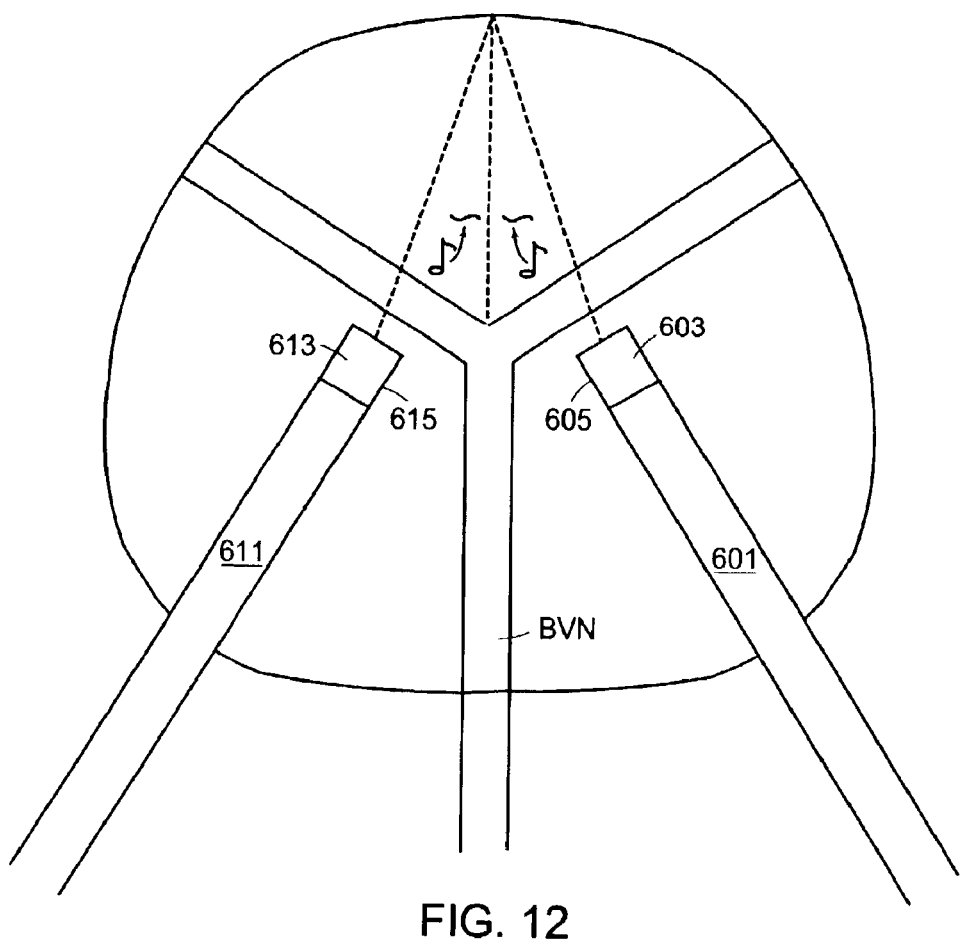
FIG. 12 depicts a top view of the treatment of the BVN with a bipolar electrode apparatus of the present invention wherein the distal ends of the probes are located substantially at the midline of the vertebral body.

In conducting initial animal experiments with a dual probe embodiment, the present inventors used a bipedicle approach as shown in FIG. 12, so that each probe approached the ION at angle δ of 45 to about 55 degrees. Since both the probes and the electrodes disposed thereon were essentially cylindrical, the inner faces 605, 615 of the electrodes produced an angle 2δ. Subsequent testing of the configuration of FIG. 12 revealed somewhat higher temperatures at the distal portion of the electrodes and somewhat lower temperatures near the proximal portions of the electrodes. Without wishing to be tied to a theory, it is believed that the shorter path between the distal regions produced a lower resistance region (as compared to more proximal inter-electrode regions) and so caused current to preferentially follow the path of the least resistance between the distal portions. Accordingly, the present inventors sought to improve upon the relatively uneven temperature profile produced by the electrode design of FIG. 12.

In accordance with the present invention, the present inventors modified its electrode design to reduce the angle 2δ produces by the inner faces, so that the distance between the proximal end of the electrodes is more equal to the distance between the proximal end of the electrodes (i.e., the faces are more parallel). When the electrodes are provided in such a condition, their orientation reduces the significance of any path of least resistance, and so current flows more evenly across the face of each electrode, thereby providing even heating and greater control over the system.

Therefore, in accordance with the present invention, there is provided an intraosseous nerve denervation device, comprising:
a) a first probe having an active electrode and a first lead,
b) a second probe having a return electrode and a second lead,
c) means for creating first and second bores within a bone for accommodating the first and second probes,
d) a power supply capable of generating a voltage difference between the active and return electrodes, the supply having third and fourth leads,
wherein the first and third leads are in electrical connection, and the second and fourth leads are in electrical connection.

Preferably, the electrodes are disposed so that the angle 2δ produced by the inner faces is less than 60 degrees, more preferably no more than 30 degrees. Still more preferably, the angle is less than 1 degree. Most preferably, the inner faces are substantially parallel.

Figure 15:
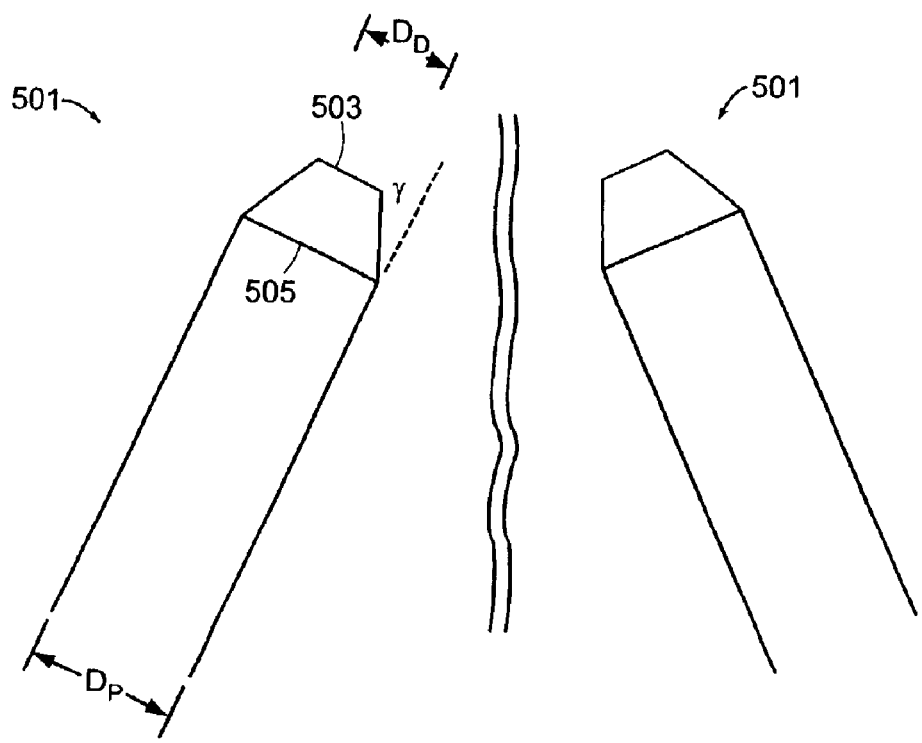
FIGS. 15–18 discloses four embodiments of the present invention in which at least a portion of the electrode faces thereof are disposed in a substantially parallel relation.

Now referring to FIG. 15, in some embodiments, substantially parallel electrodes are provided by using conical electrodes 501 that taper distally. In this FIG. 15, each cone electrode 501 has a distal end 503 having a diameter $D_D$ and a proximal end 505 having a diameter $D_P$, wherein the distal end diameter $D_D$ is larger than the proximal end diameter $D_P$. Preferably, the angle γ of the cone taper is substantially equal to the angle δ. In this condition, the inner faces of the conical electrodes will be essentially parallel to each other.

Therefore, in accordance with the present invention, there is provided intraosseous nerve denervation system comprising:
a) a first probe having a first electrode and a first lead in electrical connection with the first electrode,
wherein the first electrode has a proximal end having a proximal diameter and a distal end having a distal diameter, and the proximal end diameter is less than the distal end diameter,
and
b) a second probe having a first electrode and a first lead in electrical connection with the first electrode,
wherein the first electrode has a proximal end having a proximal diameter and a distal end having a distal diameter, and the proximal end diameter is less than the distal end diameter, and
wherein the first and second electrode are disposed so that the electrodes are parallel.

In FIG. 10, the conical shapes are frustoconical (i.e., they are portions of a cone). Frustoconical electrodes are desirable in situations where tissue charring needs to be avoided, as the relatively large diameter of the distal end of the electrode can not provide an avenue for high current density (relative to the proximal end of the electrode). Frustoconical electrodes are also desirable in situations where the probes are disposed at a relatively high angle δ, wherein the use of sharp tipped electrodes would substantially shorten the distance between the distal tips of the electrodes and thereby create an undesirable path of significantly less resistance.

In some embodiments, the frustoconical electrode is shaped so that the diameter of its distal end $D_D$ is between about 10% and 25% of the diameter of its proximal end $D_P$. In some embodiments, the frustoconical nature of the electrode is provided by physically severing the sharp distal end of the electrode. In others, the frustoconical nature of the electrode is provided by insulating the sharp distal end of an electrode.

As noted above, when the probes are placed such that their corresponding electrodes are parallel to each other, the electric field produced by electrode activation is substantially uniform between the distal and proximal portions of the electrodes. However, as the probes are oriented at an angle from parallel, the electric field becomes strongest where the electrodes are closer together. In order to compensate for this nonuniform electric field, in some embodiments of the present invention, the distal ends of the electrodes are tapered. In this tapered state, the regions of the electrodes that are closer together (e.g., the tip) also have a smaller surface area (thereby reducing the electric field in that region), while the regions of the electrodes that are farther apart (e.g., the trunk) have a larger surface area (thereby increasing the electric field in that region). Typically, the effect is largely determined by the cone size, electrode spacing and tissue type therebetween.

Figure 16:
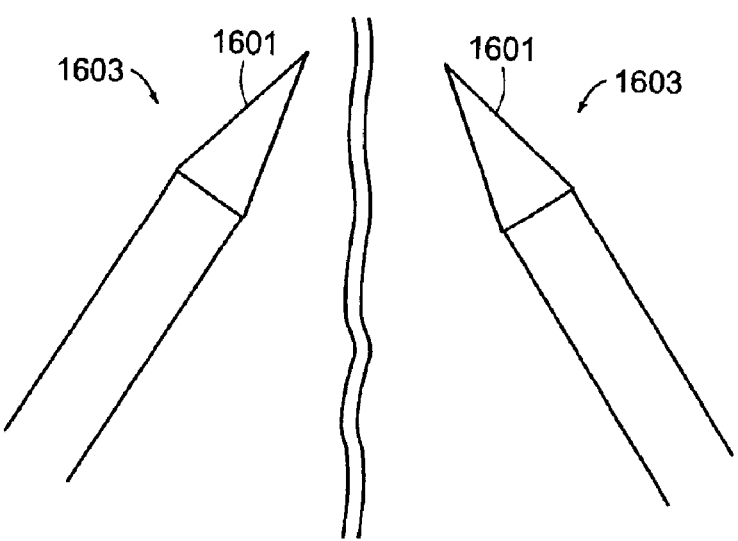

In some preferred embodiments of the tapered electrode, and now referring to FIG. 16, the distal end of the electrode terminates in a sharp tip, so that the electrode has a more completely conical shape. Preferably, the conical electrode is shaped so that the diameter of its distal end is no more than 20% of the diameter of its proximal end, more preferably no more than 10%, more preferably no more than 1%. In addition to compensating for non-uniformity in the electric field, the sharp tip may also be adapted to penetrate the cortical shell of the vertebral body.

Figure 17:
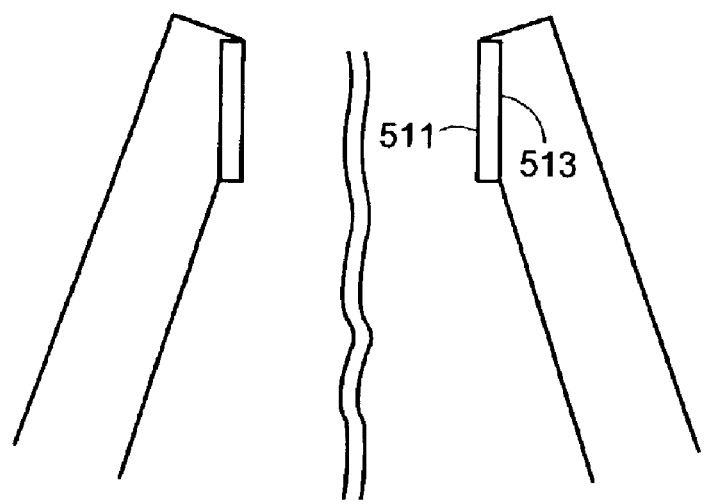

Now referring to FIG. 17, in some embodiments, current flows through an electrode having only a portion of the conical or frusto-conical shape. When electrodes of this embodiment, termed "sectored cones" face each other, their use is advantageous because they insure that current will flow the least distance, and so provide efficiency. The sectored cones of this embodiment can be produced by first manufacturing planar electrodes 511 and placing the planar electrode upon a conveniently angled probe surface 513. Alternatively, this embodiment can be produced by first manufacturing the conical electrode configuration of FIG. 15, and then masking a portion of the conical electrode with an insulating material. Unlike the embodiment of FIG. 15, this sectored cone embodiment requires careful alignment of the electrode faces and may require in vivo rotation of the electrodes to achieve the desired alignment.

Figure 18:
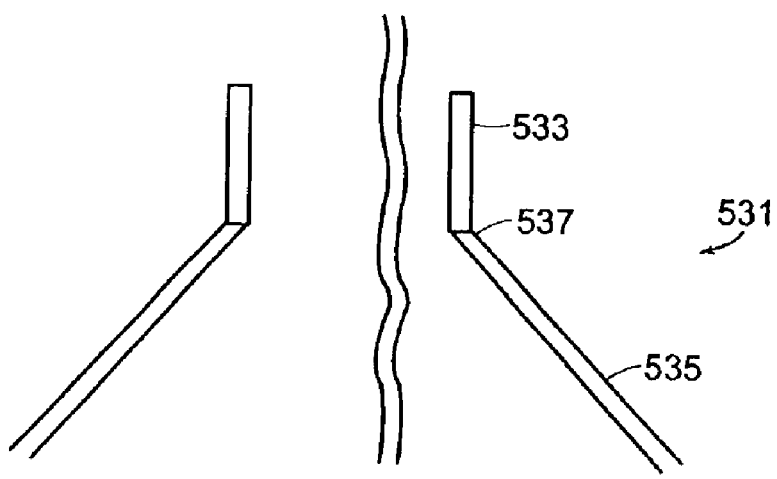

Now referring to FIG. 18, in other embodiments, substantially parallel electrodes can be provided by using elbowed probes 531. The elbowed probes have a distal end 533 and a proximal end 535 meeting at an elbow 537. In some embodiments, the elbow may be produced during the manufacturing process (thereby requiring a smaller diameter probe in order to fit through the cannula). In other embodiments, the elbow is produced in vivo, such as through use of a pull-wire, a pivot or a memory metal disposed within the probe.

Figure 19:
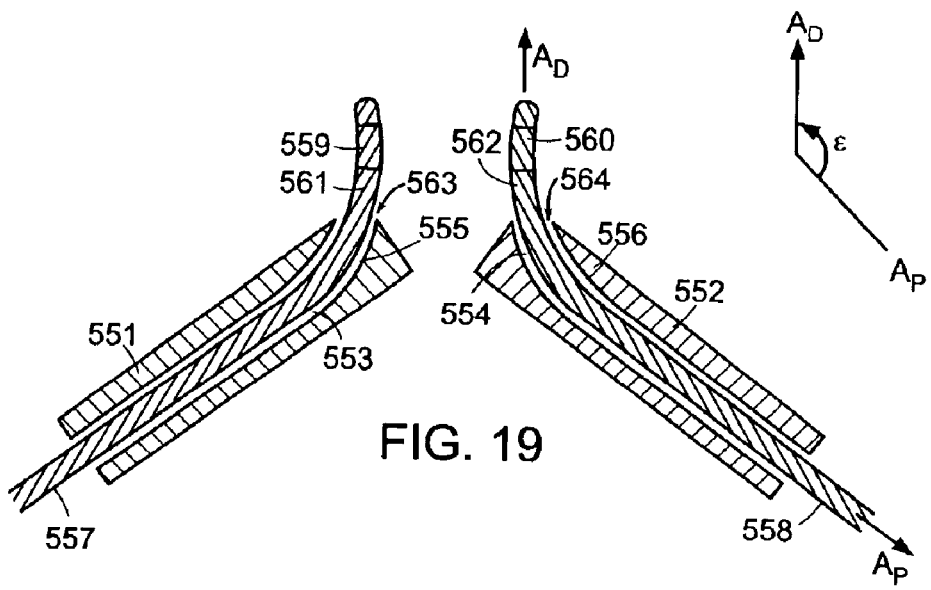
FIG. 19 discloses a cross-sectional view of an apparatus of the present invention in which the cannula has a bore having a distal bend and a lateral opening.

Now referring to FIG. 19, in some embodiments, first 551 and second 552 cannulae are each provided with a curved bore 553, 554 forming distal lateral openings 563, 564 in their respective distal end portions 555, 556. When flexible probes 557, 558 containing an electrode 559, 560 are passed through the curved bore, the distal end 561, 562 of the probe likewise conforms to the curved bore, thereby forming an intra-probe angle ε determined by the proximal $A_P$ and distal $A_D$ axes of the probe. Preferably, this intra-probe angle is between 90 and 135 degrees. Preferably, the intra-probe angle is selected so that the distal axes $A_D$ of the probes exiting the cannulae form an angle of no more than 30 degrees, preferably no more than 10 degrees, more preferably form a substantially parallel relation.

Therefore, in accordance with the present invention, there is provided an intraosseous nerve denervation system, comprising:
a) a cannula having a longitudinal bore defining a first axis,
b) a stylet having an outer diameter adapted to be received within the longitudinal bore and a distal tip adapted to penetrate cortical bone, and
c) a first probe comprising:
d) an outer diameter adapted to be received within the longitudinal bore, and
   i) a first electrode, and
   ii) a lead in electrical connection with the first electrode.

Figure 20A:
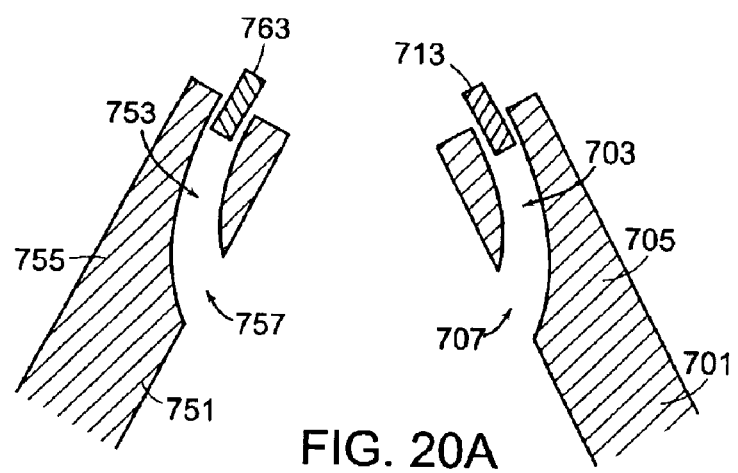
FIGS. 20a and 20b disclose cross-sectional views of an apparatus of the present invention in which the cannula has a proximal bend.
Figure 20B:
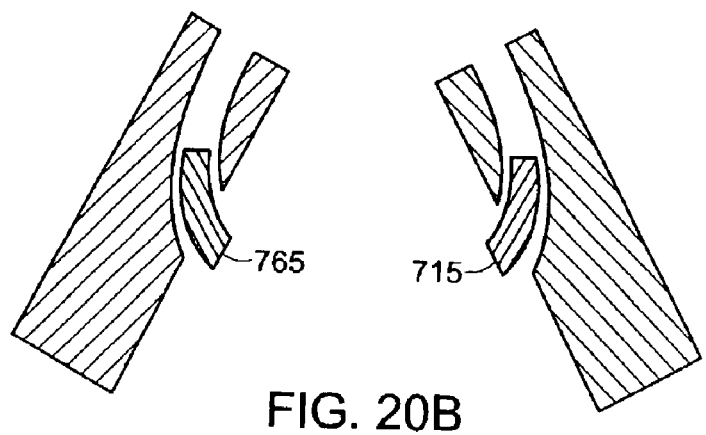

Now referring to FIGS. 20a and 20b, in some embodiments, first 701 and second 751 cannulae are each provided with a curved bore 703, 753 in their respective distal portions 705, 755, wherein each bore has a proximal lateral opening 707, 757. The apparatus further comprises first and second probes 711, 761, each containing an electrode 713, 763. In some embodiments, the probe may sit in a distal region of the bore (as in FIG. 20a) during advance of the cannula. Once the target tissue region is reached, then probes are moved proximally (by, for example, a pull wire—not shown) and exit the proximal lateral openings so that the inner faces 715, 765 of the electrodes face other.

Therefore, in accordance with the present invention, there is provided an intraosseous nerve denervation system, comprising:
a) a cannula having a longitudinal bore defining a first axis,
b) a stylet having an outer diameter adapted to be received within the longitudinal bore and a distal tip adapted to penetrate cortical bone, and
c) a first probe comprising:
   i) an outer diameter adapted to be received within the longitudinal bore, and
   ii) a first electrode, and
   iii) a lead in electrical connection with the first electrode.

Figure 21A:
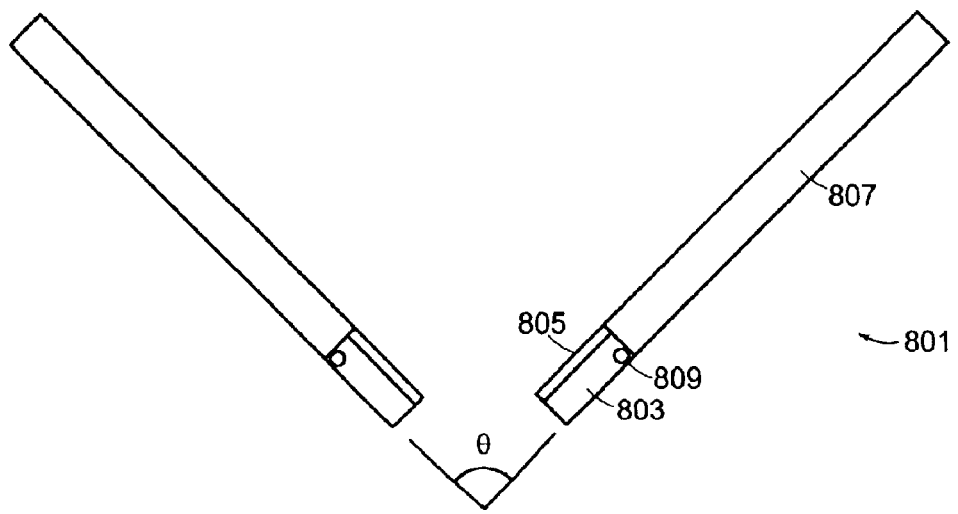
FIGS. 21a and 21b disclose cross-sectional views of an apparatus of the present invention in which the probe has a pivoted portion containing an electrode.
Figure 21B:
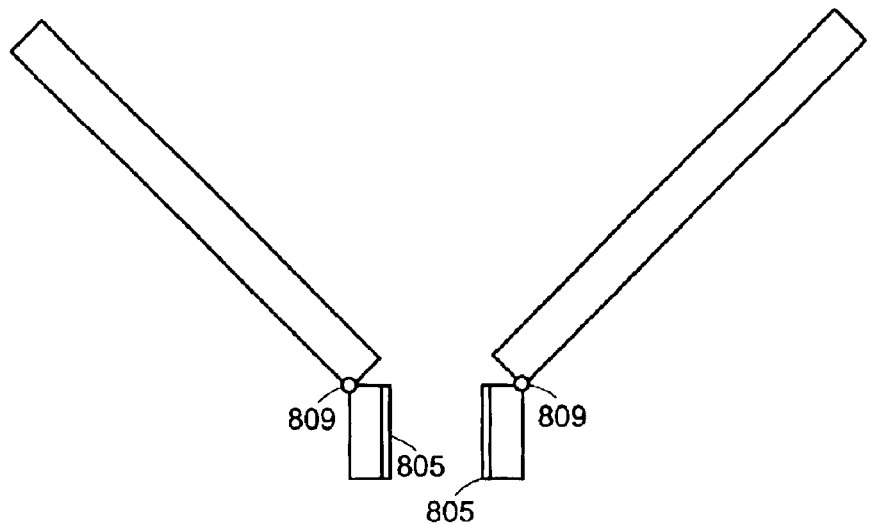

Now referring to FIG. 21a and 21b, in some embodiments, at least one probe 801 comprises i) a distal portion 803 having an electrode 805 and ii) a proximal portion 807, the distal portion being pivotally attached to the proximal portion by pivot 809. In some embodiments, two probes having such pivotally attached electrodes are introduced through the cannulae in a first linear mode (shown in FIG. 21a) to produce an angle θ between the electrodes. Next, the respective pivots are actuated (by for example, a pull wire—not shown) to produce the angled configuration shown in FIG. 21b which reduces the angle θ between the electrodes. Preferably, the pivoting brings the electrodes into a substantially parallel relation.

Therefore, in accordance with the present invention, there is provided intraosseous nerve denervation system comprising:
a) a first probe having:
   i) a distal portion having a first electrode,
   ii) a proximal portion comprising a first lead in electrical connection with the first electrode, and
   iii) a pivot pivotally connecting the proximal and distal portions of the probe.

Figure 22:
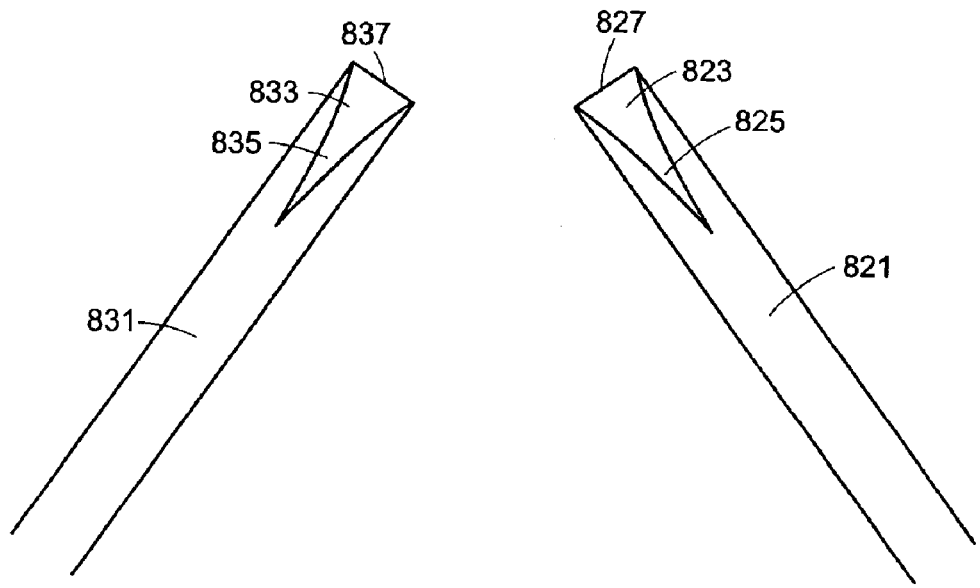
FIG. 22 discloses a probe of the present invention having reverse conical electrodes.

In some embodiments, relatively even heating is provided by providing current density gradients. Now referring to FIG. 22, in some embodiments, first 821 and second 831 probes have first 823 and second 833 electrodes having a reverse conical shape. In particular, each electrode has a relatively thick distal portion 827, 837 and a relatively thin proximal portion 825, 835. When this probe is activated, it is believed that the current density of this electrode will vary axially, with a relatively high current density present at the proximal portion of each electrode (due to the smaller surface area) and a relatively low current density present at the distal portion of the electrode (due to the larger surface area). This current density gradient should provide a more even heating zone when the electrodes themselves are oriented at a significant angle, as the preference for tip heating (caused by the angled orientation of the electrodes) is substantially balanced by the higher current density at the proximal portions of the electrodes.

Therefore, in accordance with the present invention, there is provided an intraosseous nerve denervation system comprising:
a) a first probe having a first electrode and a first lead in electrical connection with the first electrode,
wherein the first electrode has a proximal end having a proximal diameter and a distal end having a distal diameter, and
wherein the proximal end diameter is less than the distal end diameter.

Figure 23:
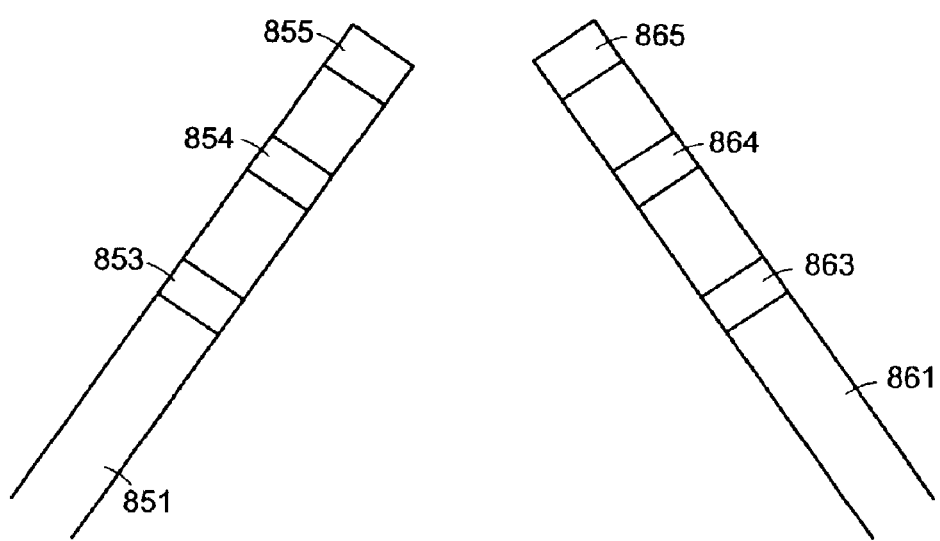
FIG. 23 discloses a probe of the present invention having a plurality of active electrodes and a corresponding plurality of return electrodes.

Current density gradients can also be produced by providing a plurality of electrodes on each probe. Now referring to FIG. 23, in some embodiments, first and second electrodes each have a plurality of electrodes. In particular, first probe 851 has first 853, second 854 and third 855 active electrodes, while second probe 861 has first 863, second 864 and third 865 return electrodes. The voltage across the probes can be selected so that there is increasing voltage (and therefore current) across the more widely spaced electrodes (i.e., $V_{855-865} < V_{854-864} < V_{853-863}$). In some embodiments, the probes of FIG. 23 are driven by multiple voltage sources (i.e., a first voltage source for providing voltage between first active electrode 853 and first return electrode 863, etc.).

Therefore, in accordance with the present invention, there is provided a method of therapeutically treating a vertebral body having a BVN, comprising the steps of:
a) providing a first energy device having distal and proximal active electrodes,
b) providing a second energy device having distal and proximal return electrodes,
c) placing the first and second energy devices in the vertebral body to define a first distance between the distal active electrode and the distal return electrode, and a second distance between the proximal active electrode and the proximal return electrode, wherein the first distance is less than the second distance,
d) applying a first high frequency voltage between the distal active and distal return electrodes, and
applying a second high frequency voltage between the proximal active and proximal return electrodes, wherein the first high frequency voltage is less than the second high frequency voltage.

Because multiple voltage sources may add complexity to the device, in other embodiments, the differences in voltage may be provided by a single voltage source by using a poorly conductive electrode. In particular, in some embodiments thereof, the probe comprises an electrically conductive probe shaft and a plurality of spaced apart insulating jackets wherein the spacing produces the electrodes of FIG. 23. In this jacketed embodiment, the probe shaft can be made of a material that is a relatively poor electrical conductor (such as tantalum) so that, when a single driving force is applied between the jacketed probes, the voltage is highest at the proximal electrode 853, but loss due to the poor conductance produces a substantially lower voltage at distal electrode 855. This jacketed embodiment eliminates the need for multiple voltage sources.

Figure 24:
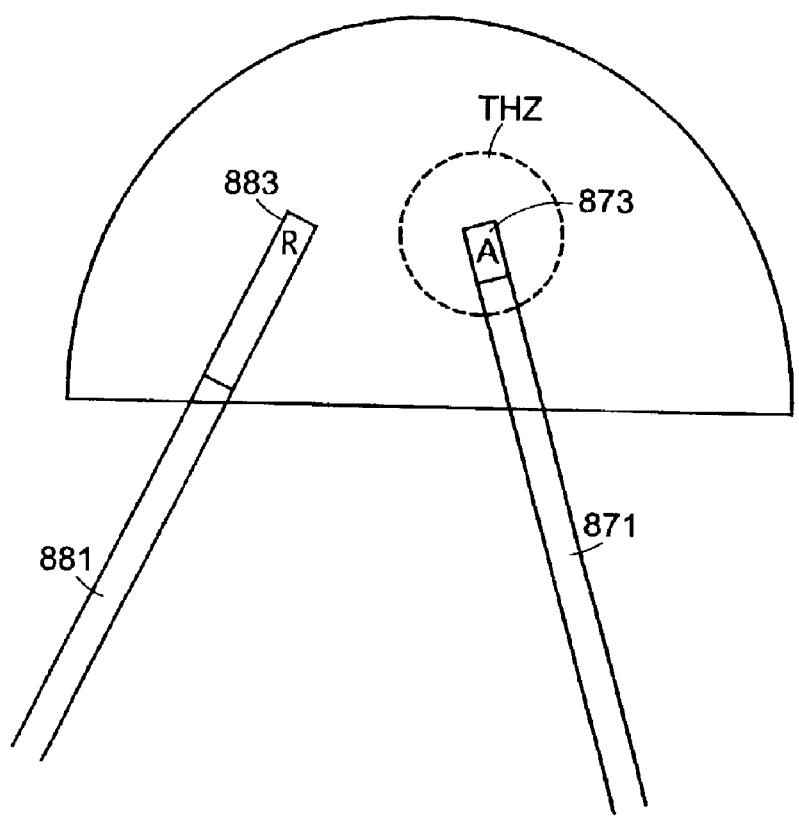
FIG. 24 discloses a bipolar probe of the present invention in which the return electrode has a relatively large surface area.

In another dual probe approach, in some embodiments, and now referring to FIG. 24, there is provided an apparatus having first probe 871 having an active electrode 873, and a second 881 probe having a return electrode 883, wherein the ratio of the surface area of the active electrode to the surface area of the return electrode is very high, i.e., at least 2:1 (more preferably at least 5:1). In this condition, the current density will be very high at the active electrode and very low at the return electrode, so that the total heating zone THZ will occur essentially only around the active electrode. Since this device heats essentially only at the active electrode, this device substantially mimics the heating profile of a monopolar electrode, but provides the desirable safety feature of locally directing the current to the return electrode.

Therefore, in accordance with the present invention, there is provided an intraosseous nerve denervation system comprising:
a) a first probe having:
  i) an active electrode having a first surface area, and
  ii) a first lead in electrical connection with the first electrode,
b) a second probe having:
  i) a return electrode having a first surface area, and
  ii) a second lead in electrical connection with the second electrode,
wherein the first surface area is at least two times greater than the second surface area, and,
means for creating first and second bores within a bone for accommodating the first and second probes.

Although the dual probe approach has many benefits, in other embodiments of the present invention, an articulated probe having both active and return electrodes may be used in accordance with the present invention.

Figure 25:
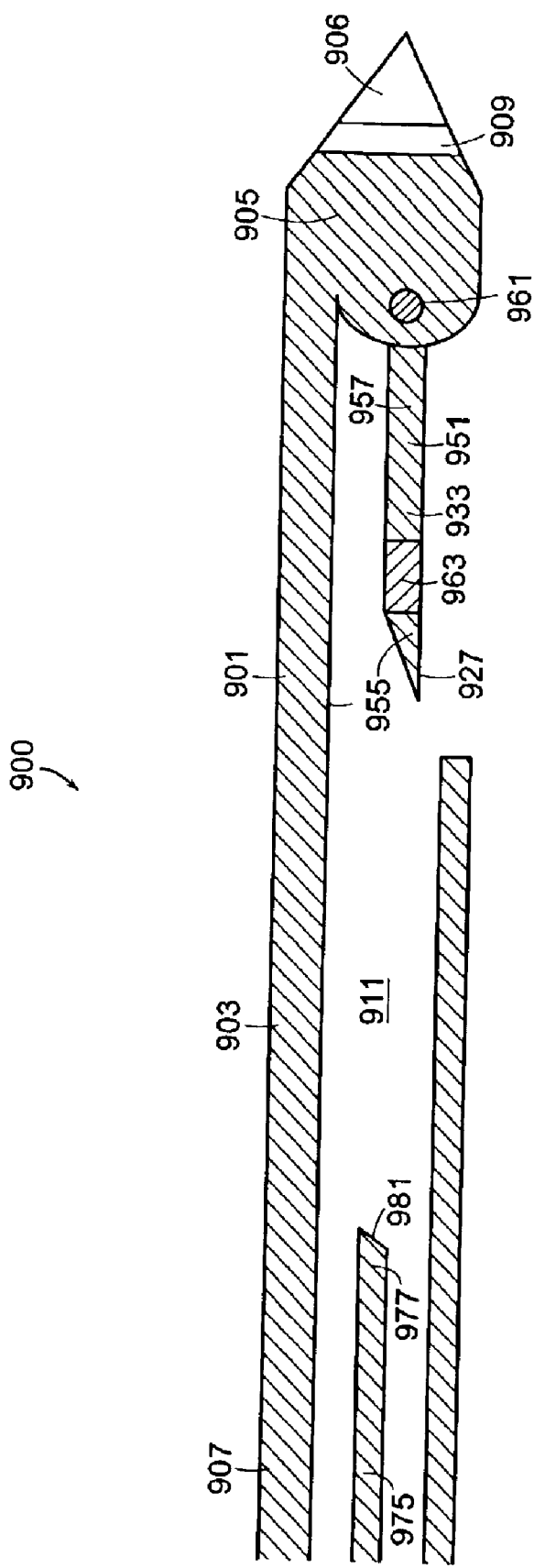
FIG. 25 presents a cross-sectional view of an articulated probe of the present invention having both active and return electrodes.

Now referring to FIG. 25, there is provided a preferred articulated device according to the present invention. In preferred embodiments, this device 900 comprises a fixed probe 901 and a pivotable probe 951.

Fixed probe 901 comprises a shaft 903 having a longitudinal axis and a distal end portion 905 comprising sharpened distal tip 906 and a proximal end portion 907. Disposed near the distal end portion of the probe is first electrode 909. The fixed probe is designed so that the first electrode is placed in electrical connection with a first lead of a power supply. In this particular embodiment, the shaft has a longitudinal bore 911 running from the proximal end portion up to at least the first electrode. Disposed within the bore is a first wire (not shown) electrically connected at its first end to the first electrode and having a second end adapted to be electrically connected to a first lead of a power supply (not shown). The fixed probe also comprises a recess 927 forming a lateral opening in the shaft and designed to house the pivotable probe when in its undeployed mode.

Pivotable probe 951 comprises a shaft 953 having a longitudinal axis, a distal end portion 955, and a proximal end portion 957 pivotally attached to the fixed probe by pivot 961. The pivot allows the pivoting probe to pivot about the fixed probe. Disposed near the distal end portion of the pivotable probe is second electrode 963. The probe is designed so that the second electrode is placed in electrical connection with a second lead of the power supply.

The pivotable probe has an undeployed mode and a deployed mode. In the un-deployed mode, the pivotable probe is seated within the recess of the fixed probe so that the axis of its shaft is essentially in line with the axis of the fixed probe shaft. In this state, the pivotable probe essentially hides within the fixed probe. In the deployed mode, the pivotable probe extends at a significant angle from the fixed probe so that the axis of its shaft forms an angle of at least 10 degrees with the axis of the fixed probe shaft.

In some embodiments, a pusher rod is used to deploy the pivotable probe. Pusher rod 975 comprises a proximal handle (not shown) for gripping and a distal end portion 977 having a shape for accessing the bore of the fixed probe. Distal end portion has a tip 981 having a shape which, when advanced distally, can push the distal end portion of the pivotable probe laterally out of the recess.

Therefore, in accordance with the present invention, there is provided a device for denervating an ION in a bone, comprising:
a) a fixed probe having a first electrode thereon in electrical connection with the powder supply, and
b) a pivotable probe comprising a second electrode having a proximal portion pivotally engaged to the fixed probe.

In some embodiments, the pivotable device has both an active and a return electrode, and the device is introduced through a single pedicle. The location of these electrodes may vary depending upon the use of the pivotable device. For example, when the active electrode is located on the pivotable probe, the return electrode may be positioned in a location selected from the group consisting of:
  a) a location on the fixed probe distal of the pivot (as in FIG. 25);
  b) a location on the fixed probe proximal of the pivot;
  c) a location on the pivotable probe located nearer the pivot; and
  d) a location on the pusher rod.

In other embodiments, the locations of the active and return electrodes are reversed from those described above.

In general, it is desirable to operate the present invention in a manner that produces a peak temperature in the target tissue of between about 80° C. and 95° C. When the peak temperature is below 80° C., the off-peak temperatures may quickly fall below about 45° C. When the peak temperature is above about 95° C., the bone tissue exposed to that peak temperature may experience necrosis and produce charring. This charring reduces the electrical conductivity of the charred tissue, thereby making it more difficult to pass RF current through the target tissue beyond the char and to resistively heat the target tissue beyond the char. In some embodiments, the peak temperature is preferably between 86° C. and 94° C.

It is desirable to heat the volume of target tissue to a minimum temperature of at least 42° C. When the tissue experiences a temperature above 42° C., nerves within the target tissue may be desirably damaged. However, it is believed that denervation is a function of the total quantum of energy delivered to the target tissue, i.e., both exposure temperature and exposure time determine the total dose of energy delivered. Accordingly, if the temperature of the target tissue reaches only about 42° C, then it is believed that the exposure time of the volume of target tissue to that temperature should be at least about 30 minutes and preferably at least 60 minutes in order to deliver the dose of energy believed necessary to denervate the nerves within the target tissue.

Preferably, it is desirable to heat the volume of target tissue to a minimum temperature of at least 50° C. If the temperature of the target tissue reaches about 50° C., then it is believed that the exposure time of the volume of target tissue to that temperature need only be in the range of about 2 minutes to 10 minutes to achieve denervation.

More preferably, it is desirable to heat the volume of target tissue to a minimum temperature of at least 60° C. If the temperature of the target tissue reaches about 60° C., then it is believed that the exposure time of the volume of target tissue to that temperature need only be in the range of about 0.01 minutes to 1.5 minutes to achieve denervation, preferably 0.1 minutes to 0.25 minutes.

Typically, the period of time that an ION is exposed to therapeutic temperatures is in general related to the length of time in which the electrodes are activated. However, since it has been observed that the total heating zone remains relatively hot even after power has been turned off (and the electric field eliminated), the exposure time can include a period of time in which current is not running through the electrodes.

In general, the farther apart the electrodes, the greater the likelihood that the ION will be contained within the total heating zone. Therefore, in some embodiments, the electrodes are placed at least 5 mm apart, more preferably at least 10 mm apart. However, if the electrodes are spaced too far apart, the electric field takes on an an undesirably extreme dumbbell shape. Therefore, in many preferred embodiments, the electrodes are placed apart a distance of between 5 mm and 25 mm, more preferably between 5 mm and 15 mm, more preferably between 10 mm and 15 mm.

In some embodiments, it is desirable to heat the target tissue so that at least about 1 cc of bone tissue experiences the minimum temperature. This volume corresponds to a sphere having a radius of about 0.6 cm. Alternatively stated, it is desirable to heat the target tissue so the minimum temperature is achieved by every portion of the bone within 0.6 cm of the point experiencing the peak temperature.

More preferably, it is desirable to heat the target tissue so that at least about 3 cc of bone experiences the minimum temperature. This volume corresponds to a sphere having a radius of about 1 cm.

In one preferred embodiment, the present invention provides a steady-state heated zone having a peak temperature of between 80° C. and 95° C. (and preferably between 86° C. and 94° C.), and heats at least 1 cc of bone (and preferably at least 3 cc of bone) to a temperature of at least 50° C. (and preferably 60° C.).

Therefore, in accordance with the present invention, there is provided a method of therapeutically treating a vertebral body having a BVN, comprising the steps of:
a) providing an energy device having an active and a return electrode,
a) inserting the active electrode into the vertebral body,
b) inserting the return electrode into the vertebral body, and
c) applying a sufficiently high frequency voltage difference between the active and return electrodes to generate a current therebetween to produce a total heating zone having a diameter of at least 0.5 cm and a steady state temperature of at least 50° C.

As noted above, a peak temperature below about 100° C. is desirable in order to prevent charring of the adjacent tissue, steam formation and tissue popping. In some embodiments, this is accomplished by providing the power supply with a feedback means that allows the peak temperature within the heating zone to be maintained at a desired target temperature, such as 90° C. In some embodiments, between about 24 watts and 30 watts of power is first supplied to the device in order to rapidly heat the relatively cool bone, with maximum amperage being obtained within about 10–15 seconds. As the bone is further heated to the target temperature, the feedback means gradually reduces the power input to the device to between about 6–10 watts.

If the active electrode has no active cooling means, it may become be subject to conductive heating by the heated tissue, and the resultant increased temperature in the electrode may adversely affect performance by charring the adjacent bone tissue. Accordingly, in some embodiments, a cool tip active electrode may be employed. The cooled electrode helps maintain the temperature of the electrode at a desired temperature. Cooled tip active electrodes are known in the art. Alternatively, the power supply may be designed to provided a pulsed energy input. It has been found that pulsing the current favorably allows heat to dissipate from the electrode tip, and so the active electrode stays relatively cooler.

The following section relates to the general structure of preferred energy devices in accordance with the present invention:

The apparatus according to the present invention comprises an electrosurgical probe having a shaft with a proximal end, a distal end, and at least one active electrode at or near the distal end. A connector is provided at or near the proximal end of the shaft for electrically coupling the active electrode to a high frequency voltage source. In some embodiments, a return electrode coupled to the voltage source is spaced a sufficient distance from the active electrode to substantially avoid or minimize current shorting therebetween. The return electrode may be provided integral with the shaft of the probe or it may be separate from the shaft In preferred embodiments, the electrosurgical probe or catheter will comprise a shaft or a handpiece having a proximal end and a distal end which supports one or more electrode terminal(s). The shaft or handpiece may assume a wide variety of configurations, with the primary purpose being to mechanically support the active electrode and permit the treating physician to manipulate the electrode from a proximal end of the shaft. The shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode array. The shaft will usually include a plurality of wires or other conductive elements running axially therethrough to permit connection of the electrode array to a connector at the proximal end of the shaft.

Preferably, the shaft may be a rigid needle that is introduced through a percutaneous penetration in the patient. However, for endoscopic procedures within the spine, the shaft will have a suitable diameter and length to allow the surgeon to reach the target site (e.g., a disc) by delivering the shaft through the thoracic cavity, the abdomen or the like. Thus, the shaft will usually have a length in the range of about 5.0 to 30.0 cm, and a diameter in the range of about 0.2 mm to about 10 mm. In any of these embodiments, the shaft may also be introduced through rigid or flexible endoscopes.

The probe will include one or more active electrode(s) for applying electrical energy to tissues within the spine. The probe may include one or more return electrode(s), or the return electrode may be positioned on the patient's back, as a dispersive pad. In either embodiment, sufficient electrical energy is applied through the probe to the active electrode(s) to either necrose the blood supply or nerves within the vertebral body.

The electrosurgical instrument may also be a catheter that is delivered percutaneously and/or endoluminally into the patient by insertion through a conventional or specialized guide catheter, or the invention may include a catheter having an active electrode or electrode array integral with its distal end. The catheter shaft may be rigid or flexible, with flexible shafts optionally being combined with a generally rigid external tube for mechanical support. Flexible shafts may be combined with pull wires, shape memory actuators, and other known mechanisms for effecting selective deflection of the distal end of the shaft to facilitate positioning of the electrode or electrode array. The catheter shaft will usually include a plurality of wires or other conductive elements running axially therethrough to permit connection of the electrode or electrode array and the return electrode to a connector at the proximal end of the catheter shaft. The catheter shaft may include a guide wire for guiding the catheter to the target site, or the catheter may comprise a steerable guide catheter. The catheter may also include a substantially rigid distal end portion to increase the torque control of the distal end portion as the catheter is advanced further into the patient's body. Specific deployment means will be described in detail in connection with the figures hereinafter.

In some embodiments, the electrically conductive wires may run freely inside the catheter bore in an unconstrained made, or within multiple lumens within the catheter bore.

The tip region of the instrument may comprise many independent electrode terminals designed to deliver electrical energy in the vicinity of the tip. The selective application of electrical energy is achieved by connecting each individual electrode terminal and the return electrode to a power source having independently controlled or current limited channels. The return electrode(s) may comprise a single tubular member of conductive material proximal to the electrode array. Alternatively, the instrument may comprise an array of return electrodes at the distal tip of the instrument (together with the active electrodes) to maintain the electric current at the tip. The application of high frequency voltage between the return electrode(s) and the electrode array results in the generation of high electric field intensities at the distal tips of the electrode terminals with conduction of high frequency current from each individual electrode terminal to the return electrode. The current flow from each individual electrode terminal to the return electrode(s) is controlled by either active or passive means, or a combination thereof, to deliver electrical energy to the surrounding conductive fluid while minimizing energy delivery to surrounding (non-target) tissue.

Temperature probes associated with the apparatus may preferably be disposed on or within the electrode carrier; between the electrodes (preferred in bipolar embodiments); or within the electrodes (preferred for monopolar embodiments). In some embodiments wherein the electrodes are placed on either side of the ION, a temperature probe is disposed between the electrodes or in the electrodes. In alternate embodiments, the deployable portion of the temperature probe comprises a memory metal.

The electrode terminal(s) are preferably supported within or by an inorganic insulating support positioned near the distal end of the instrument shaft. The return electrode may be located on the instrument shaft, on another instrument or on the external surface of the patient (i.e., a dispersive pad).

The close proximity of the dual needle design to the intraosseus nerve makes a bipolar design more preferable because this minimizes the current flow through non-target tissue and surrounding nerves. Accordingly, the return electrode is preferably either integrated with the instrument body, or another instrument located in close proximity thereto. The proximal end of the instrument(s) will include the appropriate electrical connections for coupling the return electrode(s) and the electrode terminal(s) to a high frequency power supply, such as an electrosurgical generator.

In some embodiments, the active electrode(s) have an active portion or surface with surface geometries shaped to promote the electric field intensity and associated current density along the leading edges of the electrodes. Suitable surface geometries may be obtained by creating electrode shapes that include preferential sharp edges, or by creating asperities or other surface roughness on the active surface(s) of the electrodes. Electrode shapes according to the present invention can include the use of formed wire (e.g., by drawing round wire through a shaping die) to form electrodes with a variety of cross-sectional shapes, such as square, rectangular, L or V shaped, or the like. Electrode edges may also be created by removing a portion of the elongate metal electrode to reshape the cross-section. For example, material can be ground along the length of a round or hollow wire electrode to form D or C shaped wires, respectively, with edges facing in the cutting direction. Alternatively, material can be removed at closely spaced intervals along the electrode length to form transverse grooves, slots, threads or the like along the electrodes. In other embodiments, the probe can be sectored so that a given circumference comprises an electrode region and an inactive region. In some embodiments, the inactive region is masked.

The return electrode is typically spaced proximally from the active electrode(s) a suitable. In most of the embodiments described herein, the distal edge of the exposed surface of the return electrode is spaced about 5 to 25 mm from the proximal edge of the exposed surface of the active electrode(s), in dual needle insertions. Of course, this distance may vary with different voltage ranges, the electrode geometry and depend on the proximity of tissue structures to active and return electrodes. The return electrode will typically have an exposed length in the range of about 1 to 20 mm.

The application of a high frequency voltage between the return electrode(s) and the electrode terminal(s) for appropriate time intervals effects modifying the target tissue.

The present invention may use a single active electrode terminal or an array of electrode terminals spaced around the distal surface of a catheter or probe. In the latter embodiment, the electrode array usually includes a plurality of independently current-limited and/or power-controlled electrode terminals to apply electrical energy selectively to the target tissue while limiting the unwanted application of electrical energy to the surrounding tissue and environment resulting from power dissipation into surrounding electrically conductive fluids, such as blood, normal saline, and the like. The electrode terminals may be independently current-limited by isolating the terminals from each other and connecting each terminal to a separate power source that is isolated from the other electrode terminals. Alternatively, the electrode terminals may be connected to each other at either the proximal or distal ends of the catheter to form a single wire that couples to a power source.

In one configuration, each individual electrode terminal in the electrode array is electrically insulated from all other electrode terminals in the array within said instrument and is connected to a power source which is isolated from each of the other electrode terminals in the array or to circuitry which limits or interrupts current flow to the electrode terminal when low resistivity material (e.g., blood) causes a lower impedance path between the return electrode and the individual electrode terminal. The isolated power sources for each individual electrode terminal may be separate power supply circuits having internal impedance characteristics which limit power to the associated electrode terminal when a low impedance return path is encountered. By way of example, the isolated power source may be a user selectable constant current source. In this embodiment, lower impedance paths will automatically result in lower resistive heating levels since the heating is proportional to the square of the operating current times the impedance. Alternatively, a single power source may be connected to each of the electrode terminals through independently actuatable switches, or by independent current limiting elements, such as inductors, capacitors, resistors and/or combinations thereof. The current limiting elements may be provided in the instrument, connectors, cable, controller or along the conductive path from the controller to the distal tip of the instrument. Alternatively, the resistance and/or capacitance may occur on the surface of the active electrode terminal(s) due to oxide layers which form selected electrode terminals (e.g., titanium or a resistive coating on the surface of metal, such as platinum).

In a preferred aspect of the invention, the active electrode comprises an electrode array having a plurality of electrically isolated electrode terminals disposed over a contact surface, which may be a planar or non-planar surface and which may be located at the distal tip or over a lateral surface of the shaft, or over both the tip and lateral surface(s). The electrode array will include at least two and preferably more electrode terminals, and may further comprise a temperature sensor. In a preferred aspect, each electrode terminal will be connected to the proximal connector by an electrically isolated conductor disposed within the shaft. The conductors permit independent electrical coupling of the electrode terminals to a high frequency power supply and control system with optional temperature monitor for operation of the probe. The control system preferably incorporate active and/or passive current limiting structures, which are designed to limit current flow when the associated electrode terminal is in contact with a low resistance return path back to the return electrode.

The use of such electrode arrays in electrosurgical procedures is particularly advantageous as it has been found to limit the depth of tissue necrosis without substantially reducing power delivery. The voltage applied to each electrode terminal causes electrical energy to be imparted to any body structure which is contacted by, or comes into close proximity with, the electrode terminal, where a current flow through all low electrical impedance paths is preferably but not necessarily limited. Since some of the needles are hollow, a conductive fluid could be added through the needle and into the bone structure for the purposes of lowering the electrical impedance and fill the spaces in the cancellous bone to make them better conductors to the needle.

It should be clearly understood that the invention is not limited to electrically isolated electrode terminals, or even to a plurality of electrode terminals. For example, the array of active electrode terminals may be connected to a single lead that extends through the catheter shaft to a power source of high frequency current. Alternatively, the instrument may incorporate a single electrode that extends directly through the catheter shaft or is connected to a single lead that extends to the power source. The active electrode(s) may have ball shapes, twizzle shapes, spring shapes, twisted metal shapes, cone shapes, annular or solid tube shapes or the like. Alternatively, the electrode(s) may comprise a plurality of filaments, rigid or flexible brush electrode(s), side-effect brush electrode(s) on a lateral surface of the shaft, coiled electrode(s) or the like.

The voltage difference applied between the return electrode(s) and the electrode terminal(s) will be at high or radio frequency, typically between about 50 kHz and 20 MHz, usually being between about 100 kHz and 2.5 MHz, preferably being between about 400 kHz and 1000 kHz, often less than 600 kHz, and often between about 500 kHz and 600 kHz. The RMS (root mean square) voltage applied will usually be in the range from about 5 volts to 1000 volts, preferably being in the range from about 10 volts to 200 volts, often between about 20 to 100 volts depending on the electrode terminal size, the operating frequency and the operation mode of the particular procedure. Lower peak-to-peak voltages will be used for tissue coagulation, thermal heating of tissue, or collagen contraction and will typically be in the range from 50 to 1500, preferably 100 to 1000 and more preferably 120 to 400 volts peak-to-peak. As discussed above, the voltage is usually delivered continuously with a sufficiently high frequency (e.g., on the order of 50 kHz to 20 MHz) (as compared with e.g., lasers claiming small depths of necrosis, which are generally pulsed about 10 to 20 Hz). In addition, the sine wave duty cycle (i.e., cumulative time in any one-second interval that energy is applied) is preferably on the order of about 100% for the present invention, as compared with pulsed lasers which typically have a duty cycle of about 0.0001%.

The preferred power source of the present invention delivers a high frequency current selectable to generate average power levels ranging from several milliwatts to tens of watts per electrode, depending on the volume of target tissue being heated, and/or the maximum allowed temperature selected for the instrument tip. The power source allows the user to select the power level according to the specific requirements of a particular procedure.

The power source may be current limited or otherwise controlled so that undesired heating of the target tissue or surrounding (non-target) tissue does not occur. In a presently preferred embodiment of the present invention, current limiting inductors are placed in series with each independent electrode terminal, where the inductance of the inductor is in the range of 10 uH to 50,000 uH, depending on the electrical properties of the target tissue, the desired tissue heating rate and the operating frequency. Alternatively, capacitor-inductor (LC) circuit structures may be employed, as described previously in U.S. Pat. No. 5,697,909. Additionally, current limiting resistors may be selected. Preferably, microprocessors are employed to monitor the measured current and control the output to limit the current.

The area of the tissue treatment surface can vary widely, and the tissue treatment surface can assume a variety of geometries, with particular areas and geometries being selected for specific applications. The geometries can be planar, concave, convex, hemispherical, conical, linear "in-line" array or virtually any other regular or irregular shape. Most commonly, the active electrode(s) or electrode terminal(s) will be formed at the distal tip of the electrosurgical instrument shaft, frequently being planar, disk-shaped, or hemispherical surfaces for use in reshaping procedures or being linear arrays for use in cutting. Alternatively or additionally, the active electrode(s) may be formed on lateral surfaces of the electrosurgical instrument shaft (e.g., in the manner of a spatula), facilitating access to certain body structures in endoscopic procedures.

The devices of the present invention may be suitably used for insertion into any hard tissue in the human body. In some embodiments, the hard tissue is bone. In other embodiments, the hard tissue is cartilage. In preferred embodiments when bone is selected as the tissue of choice, the bone is a vertebral body. Preferably, the present invention is adapted to puncture the hard cortical shell of the bone and penetrate at least a portion of the underlying cancellous bone. In some embodiments, the probe advances into the bone to a distance of at least ⅓ of the cross-section of the bone defined by the advance of the probe. In some embodiments, the present invention is practiced in vertebral bodies substantially free of tumors. In others, the present invention is practiced in vertebral bodies having tumors.

Therefore, in accordance with the present invention, there is provided a method of therapeutically treating a healthy vertebral body having a BVN, comprising the steps of:
a) providing an energy device having an active and a return electrode,
b) inserting the active electrode into the healthy vertebral body,
c) inserting the return electrode into the healthy vertebral body,
d) placing the active electrode on a first side of the healthy vertebral body and the return electrode on a second side of the healthy vertebral body, and
applying a sufficiently high frequency voltage difference between the active and return electrodes to generate a current therebetween to produce a total heating zone to therapeutically heat the BVN.

In some embodiments using two separate probes, the device of the present invention enters the hard tissue (preferably bone, more preferably the vertebral body) through two access points. In preferred embodiments, the pair of separate probes is adapted to denervate the BVN and enter through separate pedicles transpedicularly. In other embodiments, the pair of separate probes each enters the vertebral body extrapedicularly. In other embodiments, a first of the pair of separate probes enters the vertebral body extrapedicularly and the second enters the vertebral body transpedicularly. In embodiments using a single articulated device, the device enters via a single pedicle.

Figure 26:
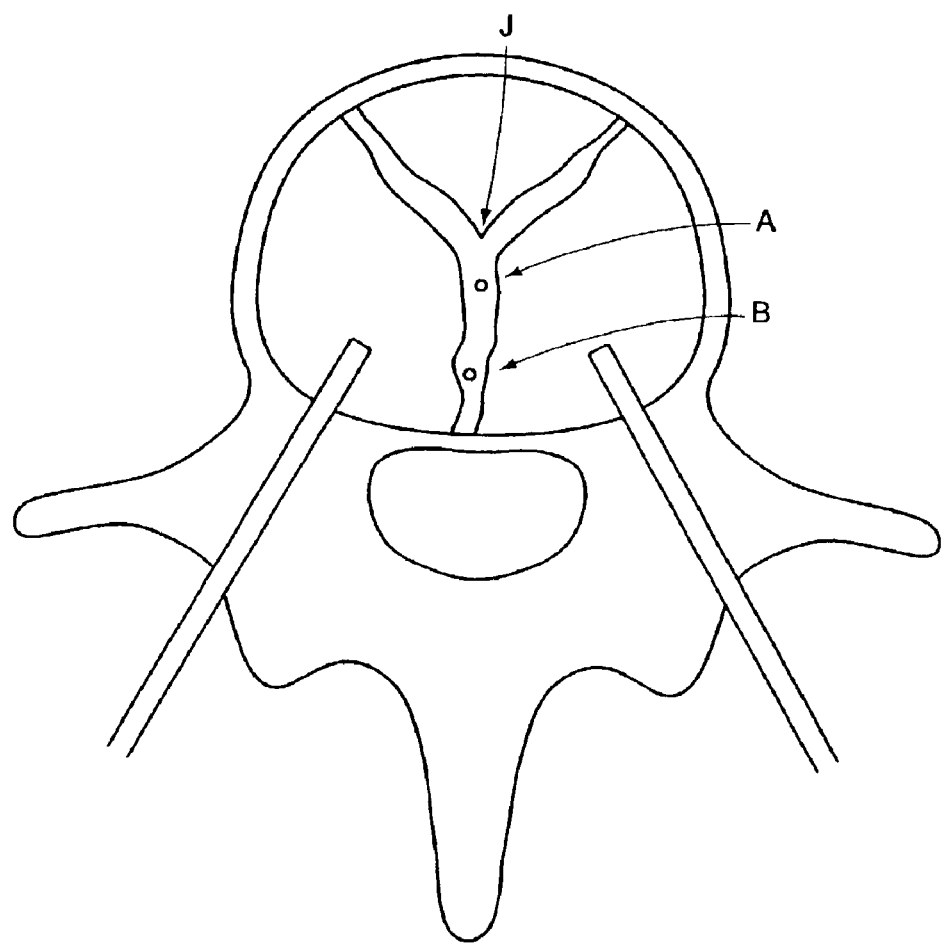
FIG. 26 discloses the treatment of a posterior portion of the BVN with a bipolar electrode apparatus of the present invention.
Figure 27A:
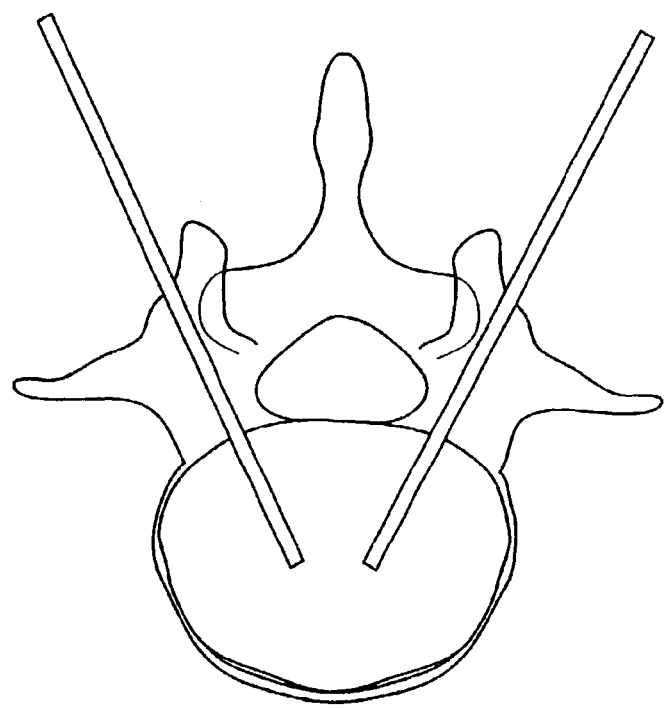
FIGS. 27a–d disclose respective top, anterior, lateral and perspective views of the placement of a bipolar electrode apparatus of the present invention within a vertebral body.
Figure 27B:
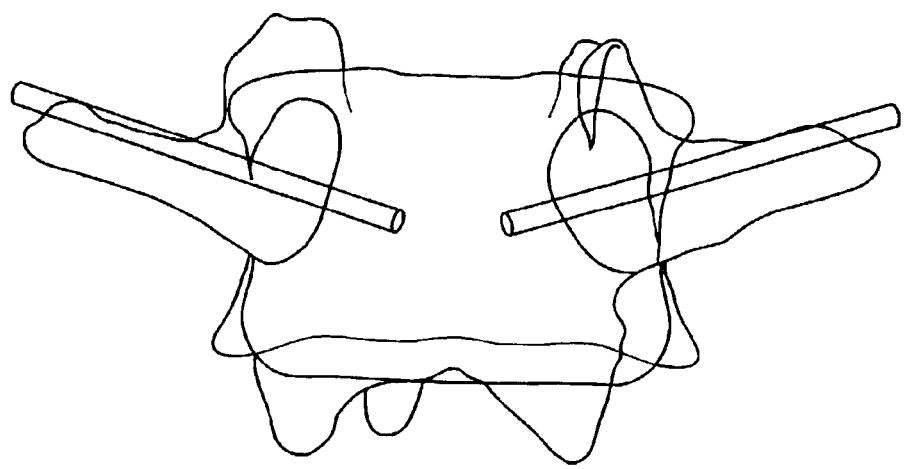
Figure 27C:
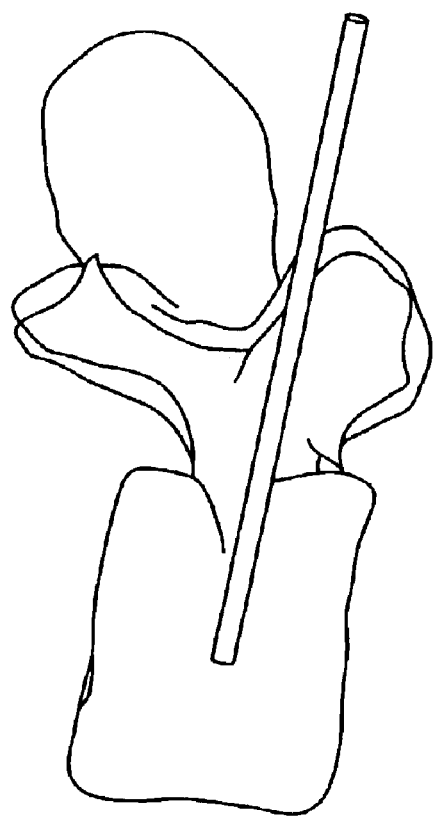
Figure 27D:
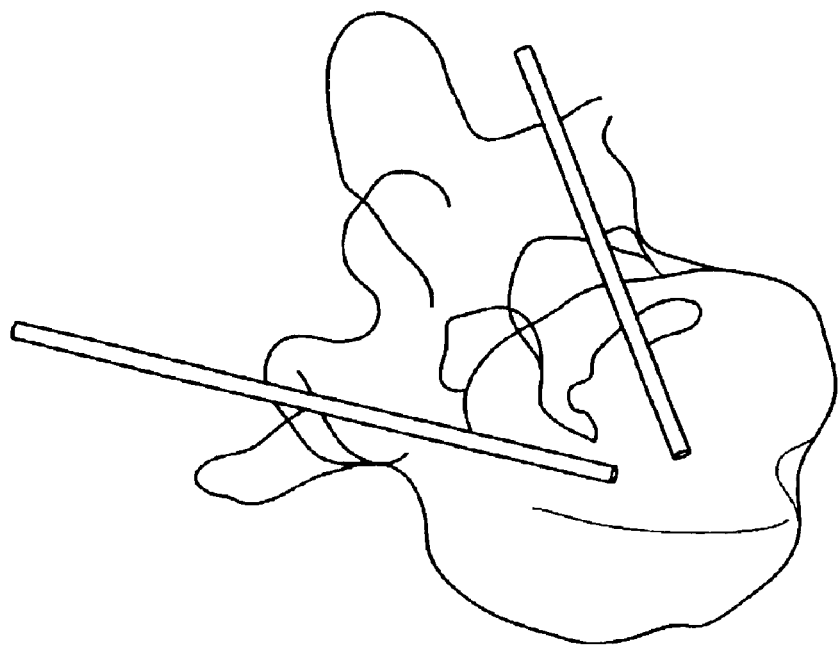

Now referring to FIG. 26, in some embodiments, the target region of the BVN is located within the cancellous portion of the bone (i.e., to the interior of the outer cortical bone region), and proximal to the junction J of the BVN having a plurality of branches. Treatment in this region is advantageous because only a single portion of the BVN need be effectively treated to denervate the entire system. In contrast, treatment of the BVN in locations more downstream than the junction require the denervation of each branch.

Therefore, in accordance with the present invention, there is provided a method of therapeutically treating a vertebral body having an outer cortical bone region and an inner cancellous bone region, and a BVN having a trunk extending from the outer cortical bone region into the inner cancellous region and a branches extending from the trunk to define a BVN junction, comprising the steps of:
a) inserting an energy device into the vertebral body, and
b) exclusively depositing energy within the inner cancellous bone region of the vertebral body between, but exclusive of the BVN junction and the outer cortical bone region, to denervate the BVN.

Typically, treatment in accordance with this embodiment can be effectuated by placing the electrodes in the region of the vertebral body located between 60% (point A) and 90% (point B) of the distance between the anterior and posterior ends of the vertebral body, as shown in FIG. 26.

EXAMPLE I

This prophetic example describes a preferred dual probe embodiment of the present invention.

First, after induction of an appropriate amount of a local anesthesia, the human patient is placed in a prone position on the table. The C-arm of an X-ray apparatus is positioned so that the X-rays are perpendicular to the axis of the spine. This positioning provides a lateral view of the vertebral body, thereby allowing the surgeon to view the access of the apparatus into the vertebral body.

Next, a cannulated stylet comprising an inner stylet and an outer cannula are inserted into the skin above each of the respective pedicles so that the distal tip of each stylet is in close proximity to the respective pedicle.

Next, the probe is advanced interiorly into the body so that the stylet tips bores through the skin, into and through the pedicle, and then into the vertebral body. The stylet is advanced until the tips reach the anterior-posterior midline of the vertebral body.

Next, the stylet is withdrawn and probe is inserted into the cannula and advanced until the first and second electrodes thereof each reach the midline of the vertebral body. The location of the two probes is shown from various perspectives in FIG. 27a–d.

Next, the power supply is activated to provide a voltage between the first and second electrodes. The amount of voltage across the electrodes is sufficient to produce an electric current between the first and second electrodes. This current provides resistive heating of the tissue disposed between the electrodes in an amount sufficient to raise the temperature of the local portion of the BVN to at least 45° C., thereby denervating the BVN.

EXAMPLE II

This example describes the efficacy of heating a large zone of a vertebral body with a bipolar energy device.

A pair of probes were inserted into a vertebral body of a porcine cadaver so that the tips of the electrodes were located substantially at the midline and separated by about 4 mm. Each electrode had a cylindrical shape, a length of about 20 mm, and a diameter of about 1.65 $mm^2$ (16 gauge) to produce a surface area of about 100 $mm^2$.

Figure 28A:
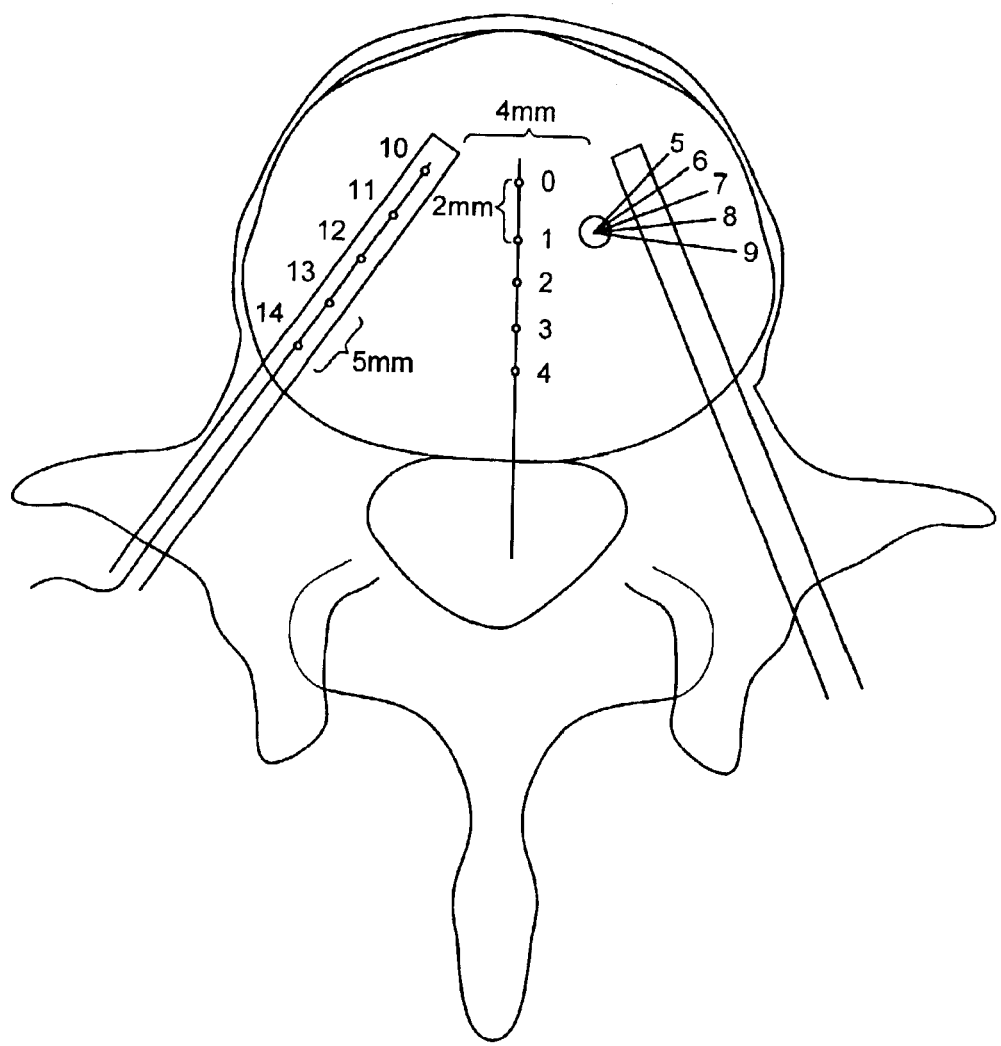

Next, and now referring to FIGS. 28a and 28b, thermocouples 0–14 were placed within the vertebral body at the 15 locations. Thermocouples 0–4 were placed halfway between the electrode tips and were separated by a distance of 2 mm. Thermocouples 5–9 were placed about at the midpoint between the probe tips, and were vertically separated by a distance of 2 mm Thermocouples 10–14 were placed along the distal portion of the probe and were separated by a distance of 5 mm.

Next, about 57 volts of energy was applied across the electrodes, and the temperature rise in the tissue was recorded at the thermocouple sites. These temperatures are provided in FIGS. 29a–c. In general, the temperature at each site rose somewhat steadily from about 22° C. to its peak temperature in about 200–300 seconds, whereupon feedback controls maintained the peak temperatures.

Figure 30A:
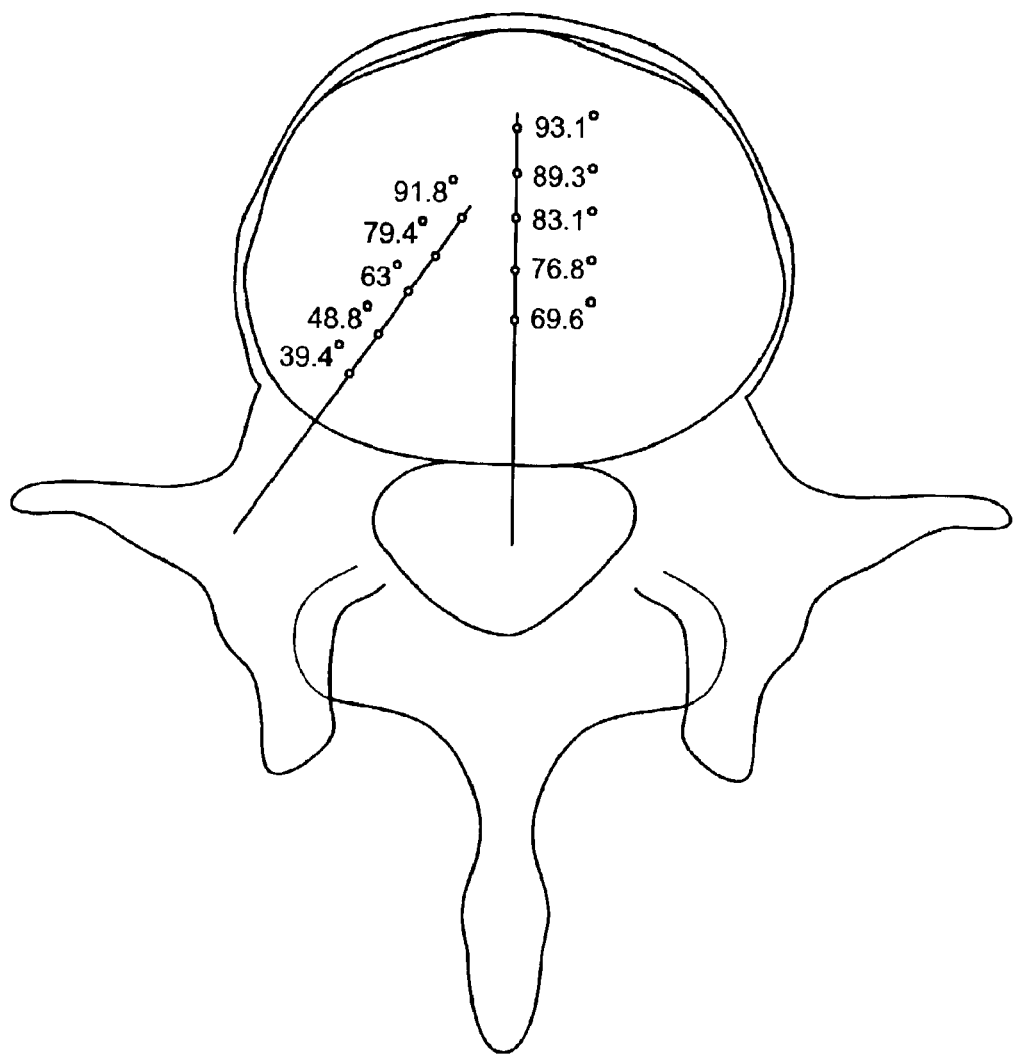
FIGS. 30a–b present the peak temperatures recorded by thermocouples T0–T14 within the vertebral body.
Figure 30B:
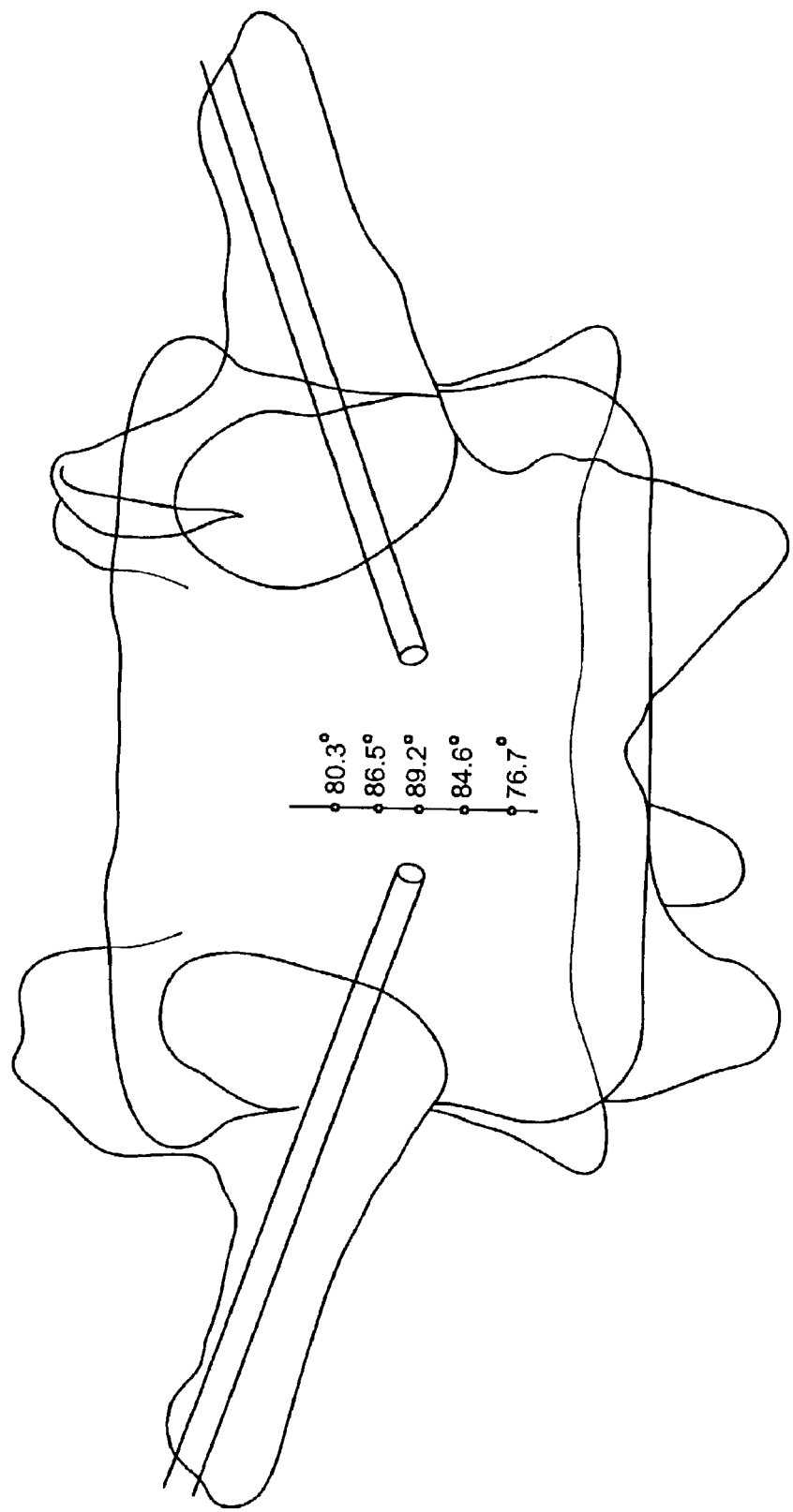

FIGS. 30a and 30b provide the peak temperatures recorded by each thermocouple. Analysis of the results in FIGS. 17a and 17b reveals that peak temperatures of between about 80° C. and 95° C. were able to be sustained over substantial distances. In particular, a temperature of 79.4 degrees was reached about 10 mm along the electrode (T11); temperatures of between 76.7 and 80.3° C. were reached at a depth of about 4 mm within the tissue (T5 and T9); and a temperature of 76.8° C. was reached about 10 mm along the electrode (T3).

The positive results provided by this example has great significance to the problem of therapeutically heating IONs, and the BVN in particular. In particular, the results of thermocouples T5–9 indicates that if an ION were located along the z-axis within 2 mm of the presumed center of the IRZ, then the ION could be sufficiently treated to at least 80° C. Similarly, the results of thermocouples T0–4 indicates that as much as a 16 mm length of ION could be sufficiently treated to at least 80° C. Lastly, the results of thermocouples T 10–14 indicate that the ION could be off-center laterally in the IRZ by as much as 2 mm and at least about 10 mm of its length could be sufficiently treated to at least 80° C.

EXAMPLE III

This embodiment describes a preferred articulated probe embodiment of the present invention.

Figure 31A:
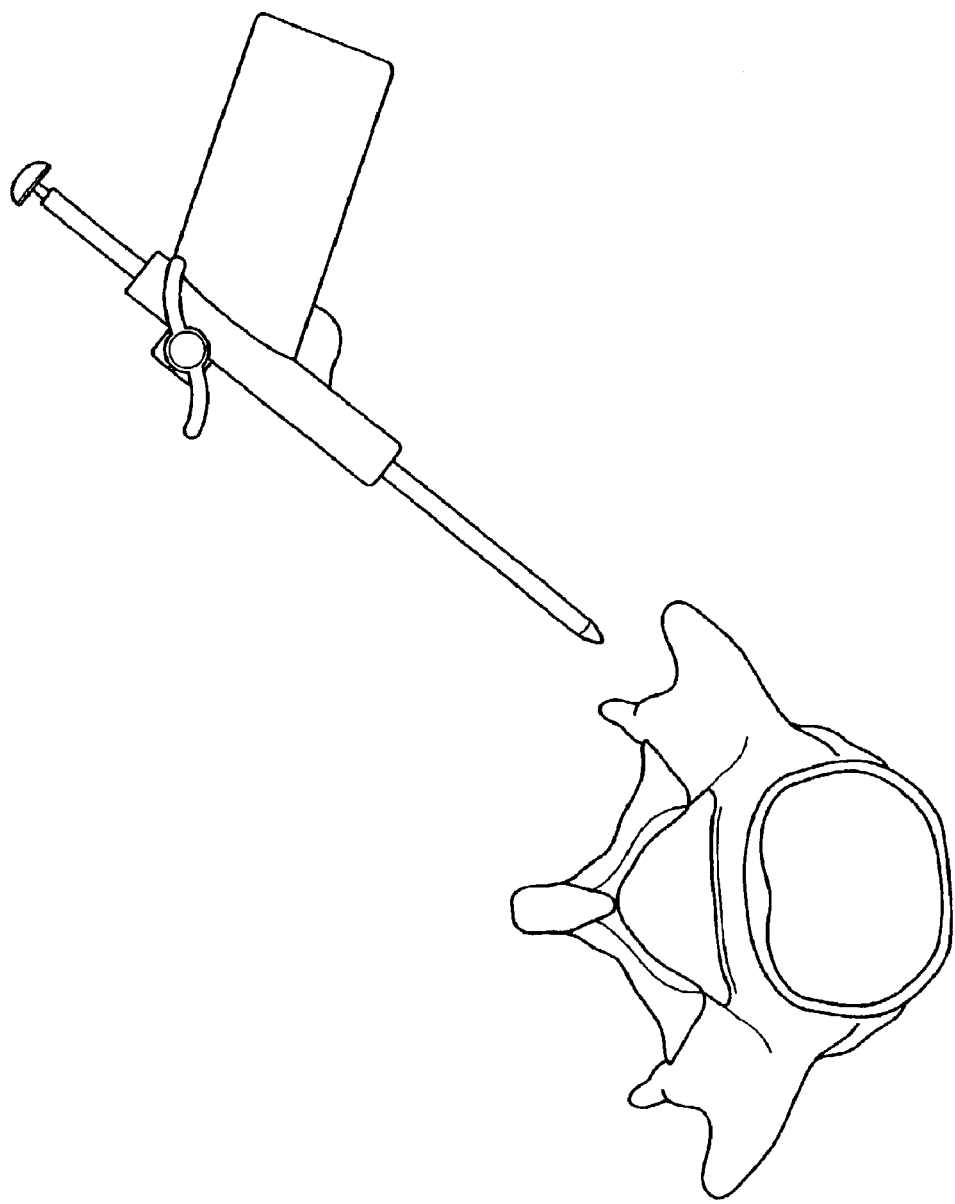
FIGS. 31a–e present top views of a preferred use of the articulated probe of FIG. 25.

The initial steps described above in Example I are carried out so that the articulated probe is poised on the patient's skin and held in place by a ratchet type gun. See FIG. 31a.

Next, the distal end of the articulated probe is inserted into the skin above a pedicle so that the distal end of the fixed probe is in close proximity to the pedicle.

Figure 31B:
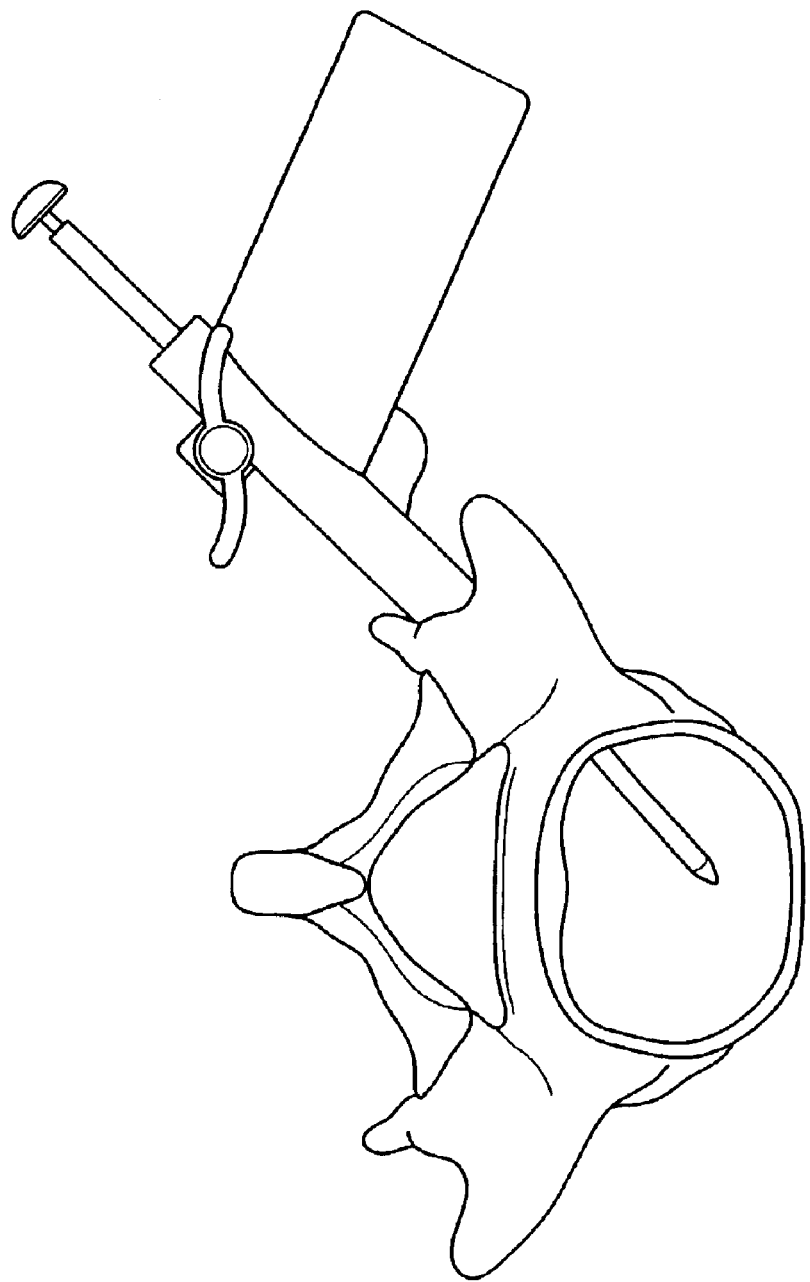

Now referring to FIG. 31b, the probe is advanced interiorly into the body so that the distal tip bores through the skin, into and through the pedicle, and then into the vertebral body. The distal tip is advanced until it reaches about 30% beyond the anterior-posterior midline of the vertebral body.

Figure 31C:
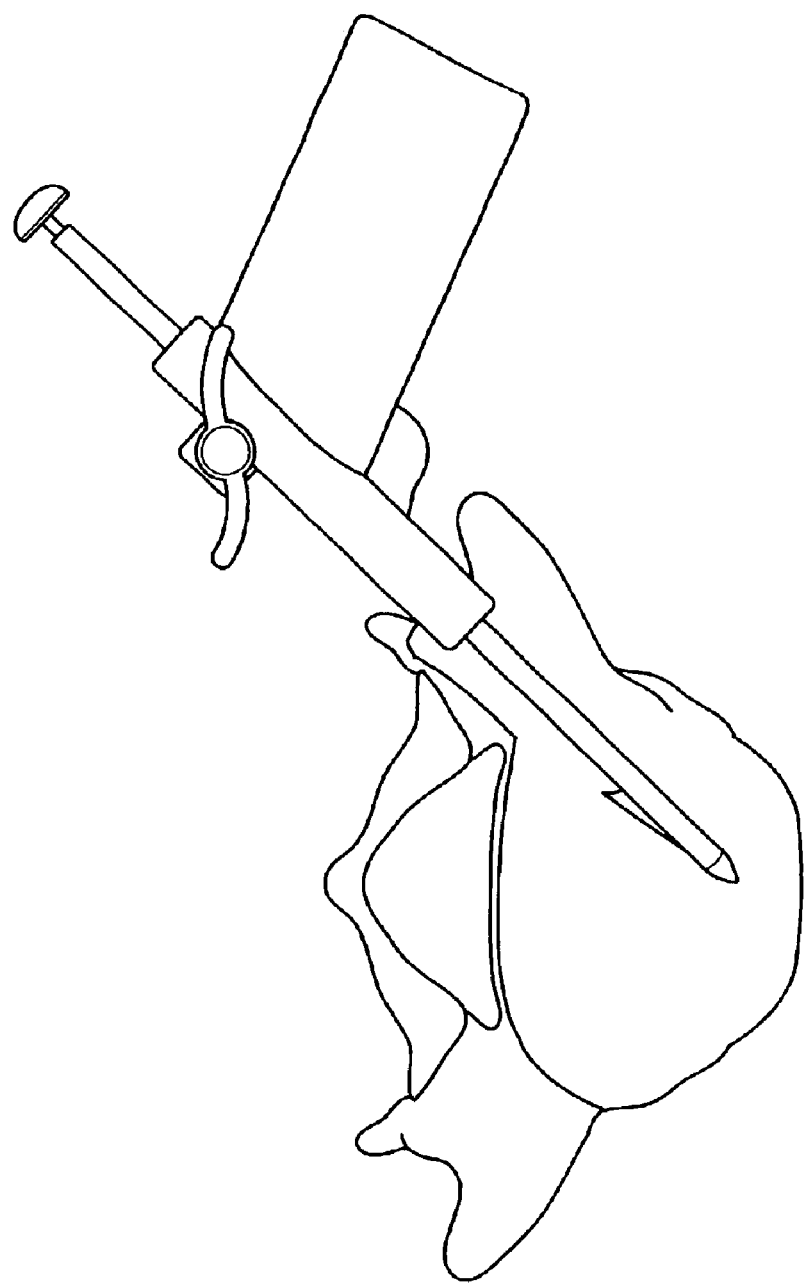

Now referring to FIG. 31c, the distal end of the pusher rod is inserted into the bore of the fixed probe and advanced until the angled portion of the pusher rod contacts the angled portion of the pivotable probe, thereby nudging the pivotable probe out of the recess. The pivotable probe is now in a partially deployed mode.

Figure 31D:
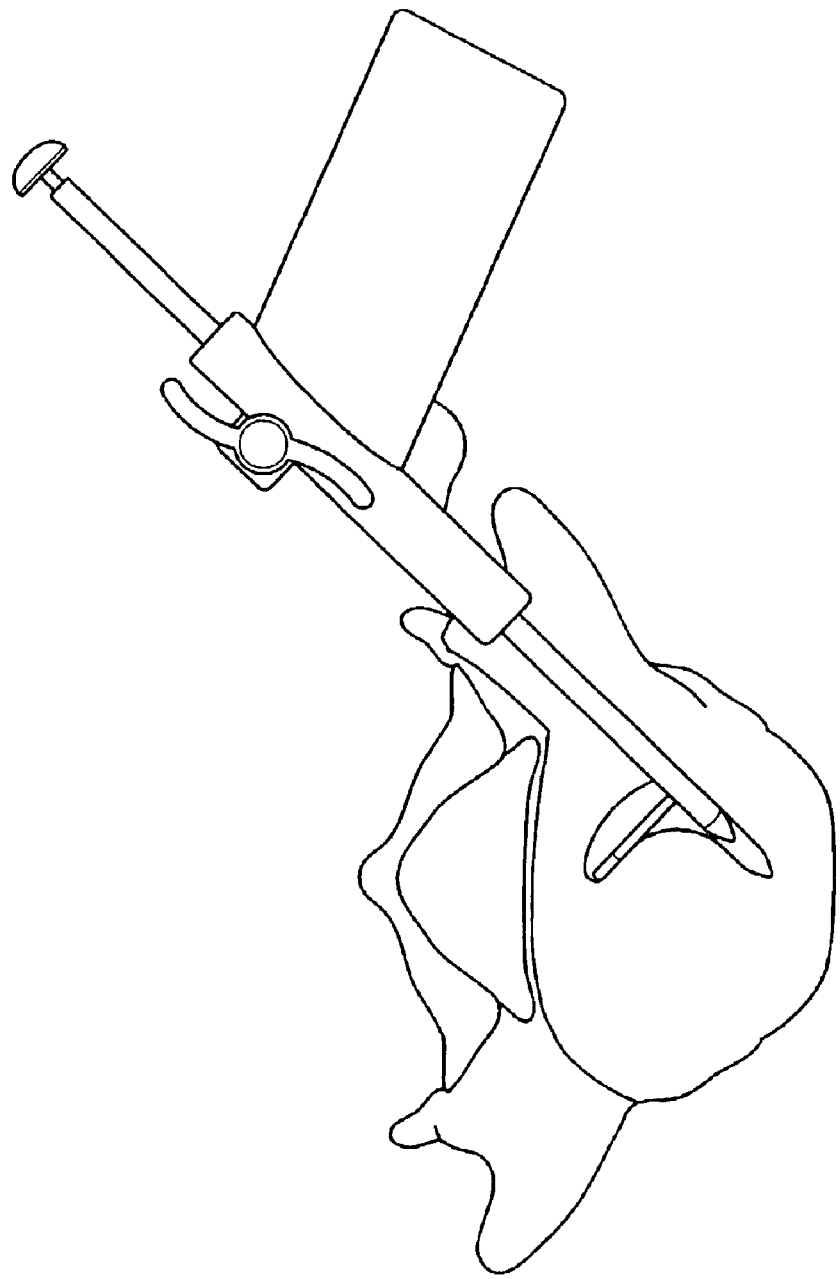

Now referring to FIG. 31d, the apparatus is slightly withdrawn from the body. As this occurs, the bone disposed between the pivotable and fixed probes prevents the pivotable probe from withdrawing along with the fixed probe, but rather forces open the pivoting means, thereby bringing the axis of the pivotable probe to a position substantially normal to the axis of the fixed probe. The pivotable probe is now in extended mode.

Next, the power supply is activated to provide a voltage between the first and second electrodes. The amount of voltage across the electrodes is sufficient to produce an electric current between the first and second electrodes. This current provides resistive heating of the tissue disposed between the electrodes in an amount sufficient to raise the temperature of the local portion of the BVN to at least 45° C., thereby denervating the BVN.

Next, the fixed probe is pushed forward to bring the pivotable probe back into the recess.

Figure 31E:
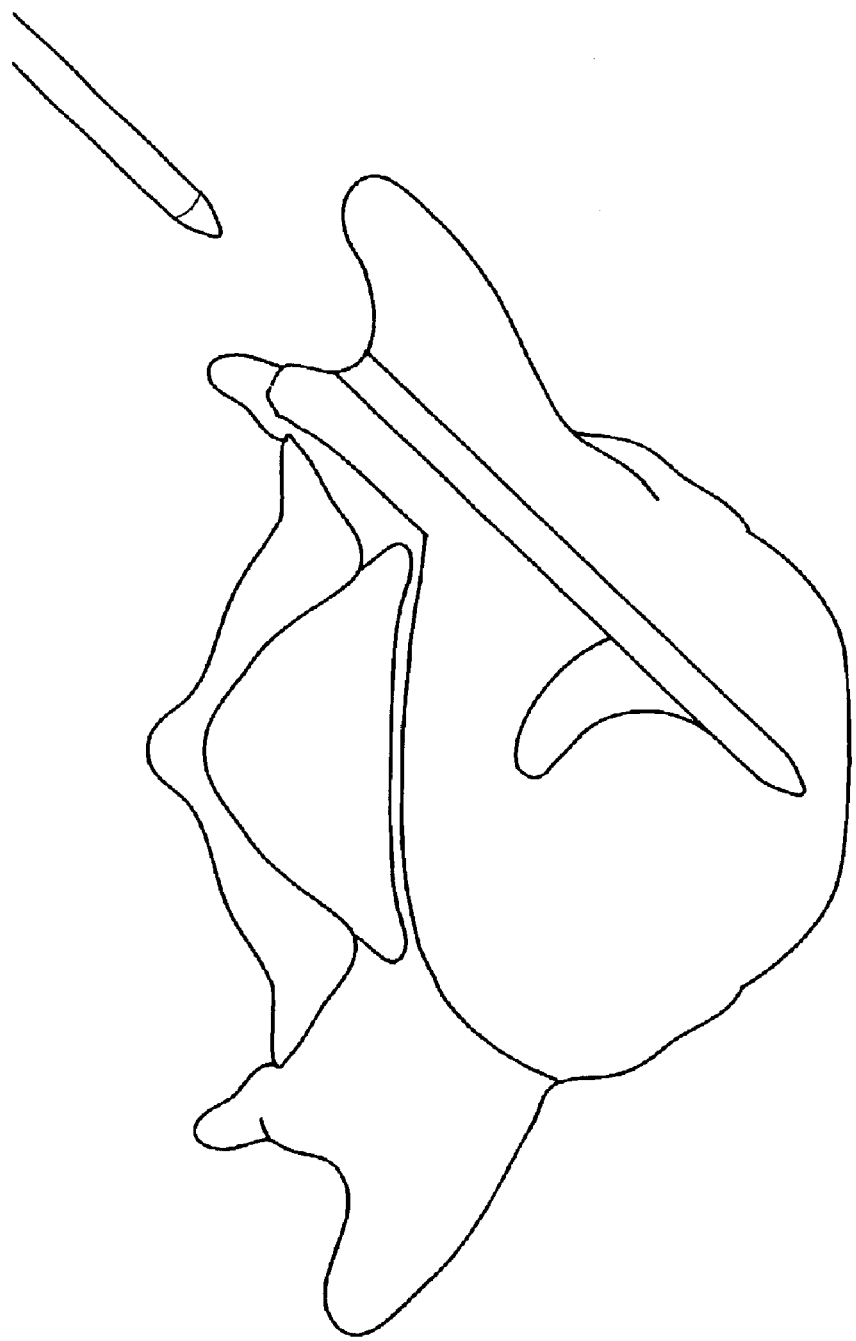

Now referring to FIG. 31e, the probe is removed from the body.

EXAMPLE IV

Figure 32:
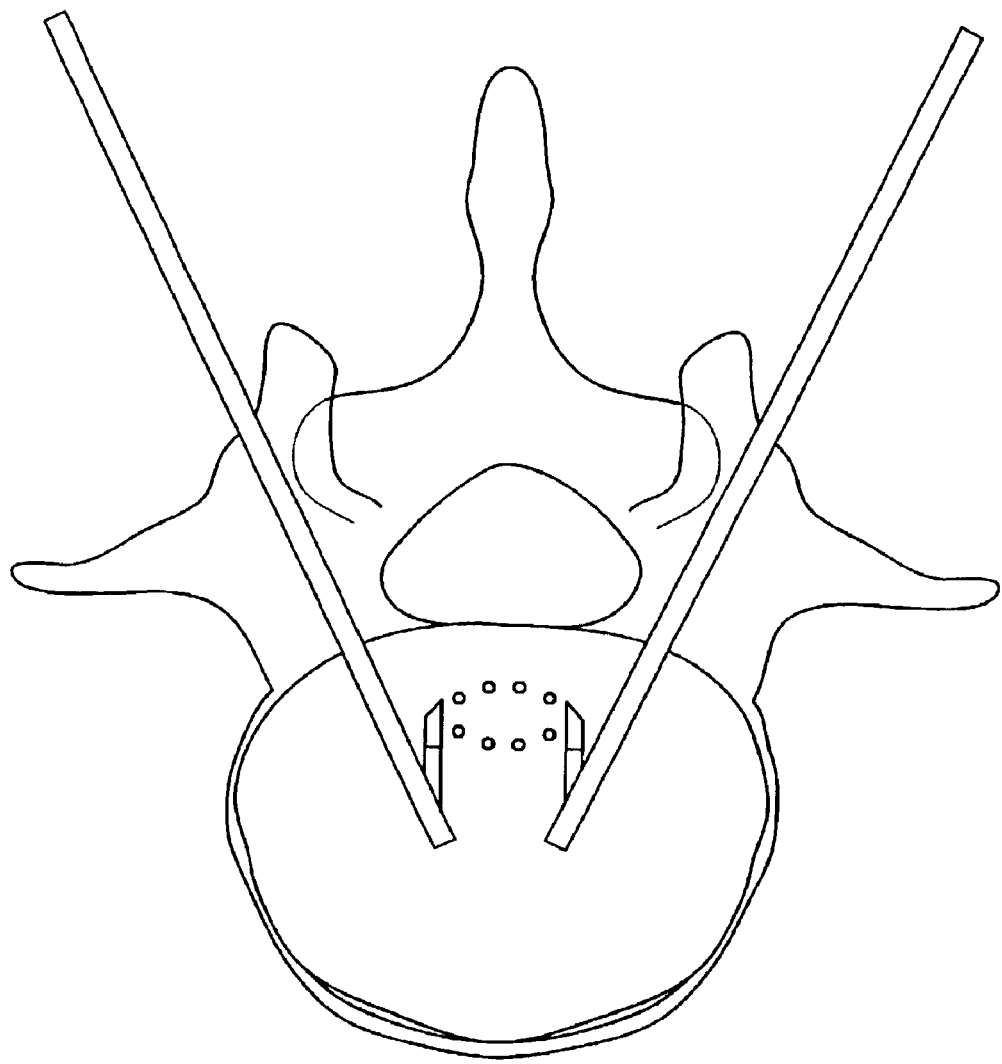
FIG. 32 presents a dual articulated needle embodiment of the present invention.

Now referring to FIG. 32, there is provided a dual articulated needle embodiment of the present invention, wherein the articulated needles are each advanced down the pedicles of the vertebral body, and each of the pivotable probes are deployed at an angle of less than 90 degrees, so that the electrodes thereon align themselves in an essentially parallel relationship. Because the electric field produced by this embodiment is relatviely even between the electrodes, the resulting total heating zone is also desirably homogeneous. Because the electrodes deploy in the central posterior portion of the vertebral body, the BVN is desirably denervated near its trunk.

We claim:

1. A method of therapeutically treating a bone having an intraosseous nerve ION defining first and second sides of the bone, comprising the steps of:
    a) inserting an energy device having an active and a return electrode into the bone,
    b) placing the active electrode on the first side of the bone and the return electrode on the second side of the bone to define a total heating zone therebetween, wherein the total heating zone comprises a resistive heating zone and a conductive heating zone, and the ION is therapeutically treated by both the resistive heating zone and the conductive heating zone, and
    c) applying a sufficiently high frequency voltage between the active and return electrodes to generate a current therebetween to resistively heat the total heating zone sufficient to denervate the ION.

2. The method of claim 1 wherein the bone is a vertebral body and the ION is a BVN.

3. The method of claim 2 wherein the bone is healthy bone.

4. The method of claim 3 wherein the resistive heating zone therapeutically heats a length $L_1$ of the ION, the total heating zone therapeutically heats a length $L_T$ of the ION, and the length $L_1$ is at least 25% of the total length LT of ION.

5. The method of claim 3 wherein the resistive heating zone has a peak temperature $T_{IR}$, the conductive heating zone has a peak temperature $T_{IC}$, and the peak temperature $T_{IR}$ of the resistive zone is no more than 15° C. greater than the peak temperature $T_{IC}$ of the conductive heating zone.

6. The method of claim 3 wherein the BVN is therapeutically treated essentially by a conductive heating zone.

7. The method of claim 6 wherein the total heating zone comprises a resistive heating zone and a conductive heating zone, and the BVN is therapeutically treated by essentially only the conductive heating zone.

8. The method of claim 7 wherein the BVN is separated from the resistive heating zone by a distance of no more than 10 mm.

9. The method of claim 6 wherein the total heating zone comprises two resistive heating zones separated by a conductive heating zone.

10. The method of claim 3 wherein the step of inserting includes a step of inserting a cannula into the bone.

11. The method of claim wherein the cannula has a bore having a stylet received therein.

12. The method of claim 11 wherein the stylet is the probe.

13. The method of claim 11 wherein the cannula is the probe.

14. The method of claim 10 wherein the cannula is withdrawn prior to insertion of the probe to create a bone hole, and the probe is inserted into the bone hole.

15. The method of claim 10 wherein the cannula is inserted into the bone prior to insertion of the probe, and the probe is inserted into the cannula bore.

16. The method of claim 3 wherein each electrode has an inner face, and the inner faces create an angle 2δ therebetween of no more than 60 degrees.

17. The method of claim 16 wherein the angle 2δ is no more than 30 degrees.

18. The method of claim 16 wherein the angle 2δ is no more than 1 degree.

19. The method of claim 3 wherein the total heating zone has a peak temperature of between 80° C. and 95° C.

20. The method of claim 3 wherein the total heating zone has a peak temperature of between 86° C. and 94° C.

21. The method of claim 3 wherein the electrodes are spaced apart by a distance of between 5 mm and 25 mm.

22. The method of claim 3 wherein the electrodes are spaced apart by a distance of between 5 mm and 15 mm.

23. The method of claim 3 wherein the electrodes are spaced apart by a distance of between 10 mm and 15 mm.

24. The method of claim 3 wherein the energy device comprises a first probe having an active electrode and a second probe having a return electrode.

25. The method of claim 3 the step of inserting comprises the steps of:

inserting a first probe having an active electrode into a first pedicle, and inserting a second probe having the return electrode into a second pedicle.

26. The method of claim 3 wherein the step of applying a voltage is sufficient to raise the minimum temperature in the total heating zone to at least 50° C. for between about 2 minutes and about 10 minutes.

27. The method of claim 3 wherein the step of applying a voltage is sufficient to raise the minimum temperature in the total heating zone to at least 60° C. for between about 0.5 minutes and about 1.5 minutes.

28. The method of claim 3 wherein the BVN has a posterior portion, and the step of applying is sufficient to denervate only the posterior portion of the BVN.

* * * * *